United States Patent [19]

Varney et al.

[11] Patent Number: 5,574,039
[45] Date of Patent: Nov. 12, 1996

[54] ANTIPROLIFERATIVE COMPOUNDS HAVING NITROGEN-CONTAINING TRICYCLIC RING SYSTEMS AND PHENYL SUBSTITUENTS

[75] Inventors: Michael D. Varney, La Costa; Gifford P. Marzoni, San Diego; Cynthia L. Palmer, La Mesa; Judith P. Deal; Terence R. Jones, both of San Diego, all of Calif.

[73] Assignee: Agouron Pharmaceuticals, Inc., La Jolla, Calif.

[21] Appl. No.: 310,387

[22] Filed: Sep. 22, 1994

Related U.S. Application Data

[62] Division of Ser. No. 583,970, Sep. 17, 1990, abandoned.

[51] Int. Cl.$^6$ .................. A61K 31/505; A61K 31/40; C07D 239/70; C07D 209/64
[52] U.S. Cl. .................. 514/257; 514/232.8; 514/255; 514/411; 544/122; 544/153; 544/249; 544/372; 548/427; 548/440; 548/441; 548/450
[58] Field of Search .................. 544/122, 249, 544/153, 372; 546/101; 548/427, 450, 440, 441; 514/232.8, 255, 257, 411

[56] References Cited

U.S. PATENT DOCUMENTS

| | | | |
|---|---|---|---|
| 3,291,808 | 12/1966 | Elslager et al. | 548/569 |
| 3,330,834 | 7/1967 | Senshu et al. | 260/281 |
| 3,347,865 | 10/1967 | Brack et al. | 548/438 |
| 3,853,913 | 12/1974 | Brack et al. | 548/438 |
| 3,959,310 | 5/1976 | Brack et al. | 548/438 |
| 3,963,747 | 6/1976 | Schefczik et al. | 548/438 |
| 4,147,865 | 4/1979 | Harnisch et al. | 544/142 |
| 4,200,752 | 4/1980 | Bertelson | 546/100 |
| 4,598,151 | 7/1986 | Kuhlthau et al. | 546/167 |
| 4,857,530 | 8/1989 | Berman et al. | 514/259 |
| 5,147,568 | 9/1992 | Luzzi et al. | 544/249 |

FOREIGN PATENT DOCUMENTS

| | | |
|---|---|---|
| 2341289 | 3/1975 | Germany . |
| 2415027 | 10/1975 | Germany . |

OTHER PUBLICATIONS

Takahashi, Chemical Abstracts, Synthesis of 3-aminonaphthostyril Derivatives and Their Antibacterial Activities, 90:186709z (1979).

Lugovskii et al., Chemical Abstracts, Synthesis of 4-(alkylamino)naphthalimides and Their Luminescence and Orientations ..., 109:210872f (1988).

Jones et al., "Quinazoline Antifolates Inhibiting Thymidylate Synthase: Variation of N$^{10}$ Substituent," J. Med. Chem. 28, 1468–1476 (1985).

Jones et al., "Quinazoline Antifolates Inhibiting Thymidylate Synthase: Variation of the Amino Acid," J. Med. Chem. 29, 1114–1118 (1986).

Jones et al., "Quinazoline Antifolates Inhibiting Thymidylate Synthase: Benzoyl Ring Modifications," J. Med. Chem. 29, 468–472 (1986).

Brixner et al., "Folate Analogues as Inhibitors of Thymidylate Synthase," J. Med. Chem. 30, 675–678 (1987).

Primary Examiner—Yogendra N. Gupta
Attorney, Agent, or Firm—Finnegan, Henderson, Farabow, Garrett & Dunner, L.L.P.

[57] ABSTRACT

The invention relates to TS-inhibiting compounds of the formula

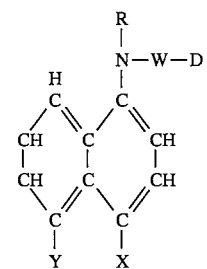

where W is an alkylene group; D is a structure having two rings that are unsubstituted or substituted, where (i) one ring is a phenyl ring and (ii) the other ring is a phenyl ring or a 6-membered heterocyclic ring; R is a hydrogen atom or an alkyl group; and X and Y together form

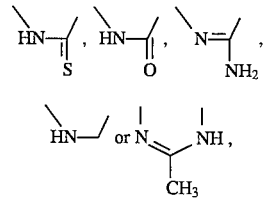

and to salts of these compounds. The moiety W can be $CH_2$, and D can be a phenyl ring bridged through a sulfonyl group to another ring.

20 Claims, No Drawings

ANTIPROLIFERATIVE COMPOUNDS HAVING NITROGEN-CONTAINING TRICYCLIC RING SYSTEMS AND PHENYL SUBSTITUENTS

CROSS-REFERENCE TO RELATED APPLICATION

This is a divisional of U.S. Ser. No. 07/583,970, filed Sep. 17, 1990 now abandoned.

FIELD OF THE INVENTION

The present invention relates to certain substituted naphthalene compounds which inhibit the enzyme thymidylate synthase ("TS"), to pharmaceutical compositions containing these naphthalene compounds, and to the use of these compounds to inhibit TS, including all effects derived from the inhibition of TS. Effects derived from the inhibition of TS include the inhibition of the growth and proliferation of the cells of higher organisms and of microorganisms, such as yeast and fungi. Such effects include antitumor activity. A process for the preparation of the substituted naphthalene compounds of the invention is also disclosed.

BACKGROUND OF THE INVENTION

The large class of antiproliferative agents includes antimetabolite compounds. A particular subclass of antimetabolites known as antifolates or "antifols" are antagonists of the vitamin folic acid. Typically, antifolates closely resemble the structure of folic acid, including the characteristic p-benzoyl glutamate moiety of folic acid. TS has long been considered an important target enzyme in the design and synthesis of antitumor agents, and a number of folate analogues have been synthesized and studied for their ability to inhibit TS. See, for example, Brixner et al., *Folate Analogues as Inhibitors of Thymidylate Synthase*, J. Med. Chem. 30, 675 (1987); Jones et al., *Quinazoline Antifolates Inhibiting Thymidylate Synthase: Benzoyl Ring Modifications*, J. Med. Chem., 29, 468 (1986); Jones et al., *Quinazoline Antifolates Inhibiting Thymidylate Synthase: Variation of the Amino Acid*, J. Med. Chem., 29, 1114 (1986); and Jones et al., *Quinazoline Antifolates Inhibiting Thymidylate Synthase: Variation of the $N^{10}$ Substituent*, J. Med. Chem. 28, 1468 (1985); and copending U.S. patent application Ser. No. 07/432,338 filed Nov. 6, 1989.

SUMMARY OF THE INVENTION

The present invention introduces a novel class of substituted naphthalene compounds which do not particularly resemble the structure of folic acid and yet, unexpectedly, inhibit the enzyme TS. The present invention also relates to pharmaceutical compositions containing these substituted naphthalene compounds and the use of these compounds to inhibit TS, including all effects derived from the inhibition of TS. Effects derived from the inhibition of TS include the inhibition of the growth and proliferation of the cells of higher organisms and of microorganisms, such as yeast and fungi. Such effects include antitumor activity. Processes for the preparation of the substituted naphthalene compounds of the invention are also disclosed.

DETAILED DESCRIPTION OF THE INVENTION

The present invention relates to antiproliferative naphthalene compounds capable of inhibiting thymidylate synthase having the formula:

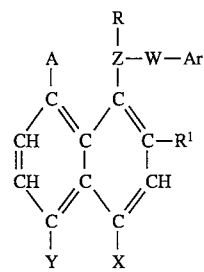

wherein:

Z and W are independently nitrogen, sulfur, or substituted or unsubstituted alkylene groups with the proviso that, when either of Z or W is nitrogen or sulfur, the other is a substituted or unsubstituted alkylene group;

Ar is a group comprising one or more rings selected from the group consisting of (1) substituted or unsubstituted aryl rings and (2) substituted or unsubstituted heterocyclic rings;

R is hydrogen or a substituted or unsubstituted alkyl group;

$R^1$ is hydrogen, a substituted or unsubstituted lower alkyl group, or a substituted or unsubstituted amino group;

A is a hydrogen, halogen, carbon, nitrogen or sulfur atom with the proviso that, when A is carbon, nitrogen or sulfur, A may itself be substituted with a substituted or unsubstituted alkyl group; and X and Y together form a nitrogen-containing, five- or six-membered heterocyclic ring which itself may be substituted or unsubstituted.

As used herein, the expression "a compound capable of inhibiting thymidylate synthase" denotes a compound with a TS inhibition constant $K_i$ of less than or equal to about $10^{-4}$M. The compounds of the invention preferably have $K_i$ values in the range of less than about $10^{-5}$M, preferably less than about $10^{-6}$, even more preferably less than about $10^{-9}$M and, most preferably, in the range from about $10^{-12}$ to about $10^{-14}$M.

Z in the above formula can be a nitrogen, sulfur, or substituted or unsubstituted alkylene group with the proviso that, when W is nitrogen or sulfur, Z is a substituted or unsubstituted alkylene group. Preferably Z is a nitrogen atom and, most preferably, is a nitrogen which, when taken with R and W, forms a tertiary amine group.

W in the above formula can be a nitrogen, sulfur, or substituted or unsubstituted alkylene group with the proviso that, when Z is nitrogen or sulfur, W is a substituted or unsubstituted alkylene group such as methylene, ethylene, hydroxyethylene, n-propylene, isopropylene, chloropropylene, and the like. Preferably, W is an unsubstituted alkylene group and, most preferably, is a methylene group.

As indicated above, Ar can be any one of a large number of ring compounds selected from the group consisting of (1) substituted or unsubstituted aryl rings and (2) substituted or unsubstituted heterocyclic rings. Examples of useful aryl ring groups include phenyl, 1,2,3,4-tetrahydronaphthyl, naphthyl, phenanthryl, anthryl, and the like. Examples of typical heterocyclic rings include 5-membered monocyclic ring groups such as thienyl, pyrrolyl, 2H-pyrrolyl, imidazolyl, pyrazolyl, furyl, isothiazolyl, furazanyl, isoxazolyl, and the like; 6-membered monocyclic groups such as pyridyl, pyranyl, pyrazinyl, pyrimidinyl, pyridazinyl, and the like; and polycyclic heterocyclic ring groups such as benzo[b]thienyl, naphtho[2,3-b]thienyl, thianthrenyl, isobenzofuranyl, chromenyl, xanthenyl, phenoxathiinyl, indolizinyl, isoindolyl, 3H-indolyl, indolyl, indazolyl, purinyl, 4H-quinolizinyl, isoquinolyl, quinolyl, phthalazinyl, naphthyridinyl, quinoxalinyl, quinazolinyl, cinnolinyl, pteridinyl, 4H-carbazolyl, carbazolyl, beta-carbolinyl, phenanthridinyl, acridinyl, perimidinyl, phenanthrolinyl, phenazinyl, isothiazlyl, phenothiazinyl, phenoxazinyl, and the like.

Preferably, Ar is a monocyclic or bicyclic, substituted or unsubstituted aryl or hetoaryl ring. More preferably, Ar is a phenyl, naphthyl or heteroaryl ring and, most preferably, is phenyl. Ar may be unsubstituted or Ar may be substituted with one or more of a wide variety of electron-donating and electron-withdrawing substituents. Typical substituents include halogen, hydroxy, alkoxy, alkyl, hydroxyalkyl, fluoroalkyl, amino, —CN, —NO$_2$, carbalkoxy, carbamyl, carbonyl, carboxyldioxy, carboxy, amino acid carbonyl, amino acid sulfonyl, sulfamyl, sulfanilyl, sulfhydryl, sulfino, sulfinyl, sulfo, sulfonamido, sulfonyl, substituted or unsubstituted phenylsulfonyl, phenylmercapto, phosphazo, phosphinico, phosphino, phospho, phosphono, phosphoro, phosphoroso,

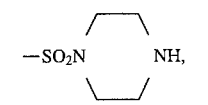

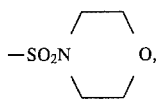

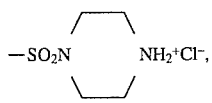

and

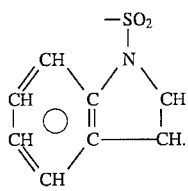

In a preferred embodiment, Ar is substituted with at least one electron-withdrawing group such as —NO$_2$, —CN, sulfonyl, carboxy, halogen, mercaptoaryl, and the like. Even more preferably, Ar is substituted with a >C=O or >SO$_2$ group such as a sulfonyl group directly bonded to a substituted or unsubstituted phenyl or heterocyclic ring. Most preferably, Ar is substituted in the para-position (i.e., the 4-position) with a sulfonylphenyl group.

It should be noted that, when Ar is a phenyl group substituted with a sulfonylphenyl group, the phenyl ring of the sulfonylphenyl group may also itself be substituted with such substituents as hydroxy, alkoxy, amino, carboxy, halogen and the like.

Particularly preferred structures for Ar include:

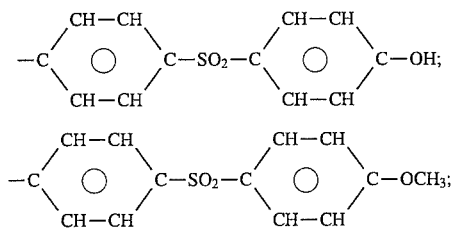

-continued

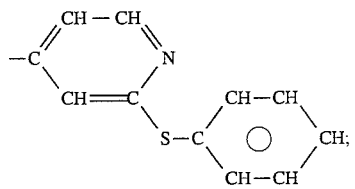

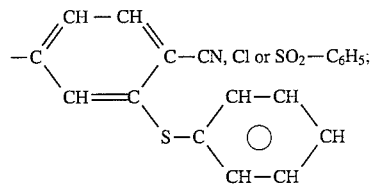

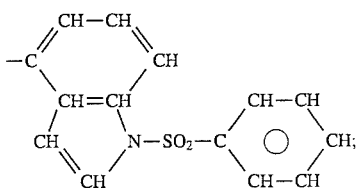

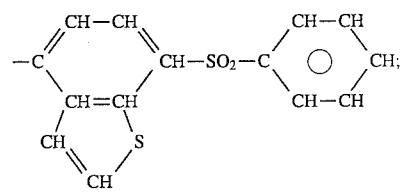

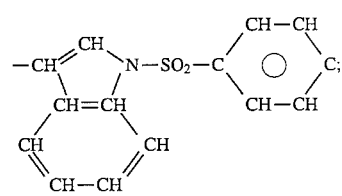

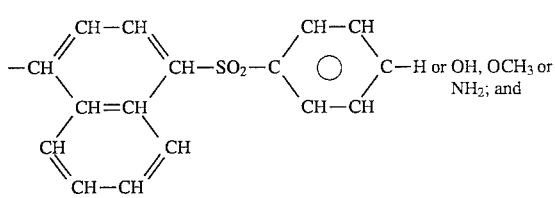

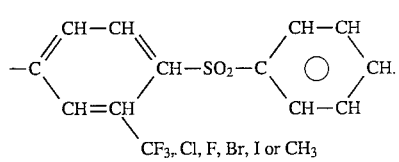

CF$_3$, Cl, F, Br, I or CH$_3$

R in the substituted naphthalene compounds of the invention can be hydrogen or any one of a large number of substituted or unsubstituted alkyl groups, such as methyl, ethyl, hydroxyethyl, n-propyl, isopropyl, hydroxypropyl, —CH$_2$—S—CH$_3$, n-butyl, tert-butyl, pentyl, hexyl and the like. Preferably, R is a lower alkyl group, such as a methyl group.

R$_1$ in the above formula can be hydrogen; a substituted or unsubstituted lower alkyl group such as methyl, ethyl, hydroxyethyl, n-propyl, isopropyl, hydroxypropyl, and the like; or a substituted or unsubstituted amino group such as —NH$_2$, methylamine, dimethylamine, trimethylamine, ethylamine, diethylamine, triethylamine, n-propylamine, di-n-propylamine, tri-n-propylamine, isopropylamine, n-butylamine, tert-butylamine, benzylamine, and the like. Preferably, R is a hydrogen atom.

A in the above formula can be a hydrogen atom; a halogen atom such as chlorine, bromine or iodine; a carbon atom which may, for example, be part of an alkyl group such as methyl, ethyl, n-propyl, isopropyl, n-butyl, tert-butyl, pentyl, or hexyl or may be part of a substituted alkyl group such as alkoxymethyl, hydroxyethyl or the like; or a nitrogen atom which may, for example, be part of a substituted or unsubstituted amino or nitro group; or a sulfur atom, for example, —SH, alkyl sulfides such as methyl sulfide, ethyl sulfide and the like. It should be noted however, that, when A is either a carbon, nitrogen or sulfur atom, A may itself be substituted with a substituted or unsubstituted alkyl group.

Preferably, A is a hydrogen, halogen or carbon atom and, even more preferably, is a hydrogen atom, a chlorine atom, or a carbon atom which, taken together with an appropriate number hydrogen atoms, forms a lower alkyl group such as a methyl group. Most preferably, A is a carbon atom which, taken together with three hydrogen atoms, forms a methyl group.

X in the above structural formula forms, with Y, a nitrogen-containing, five- or six-membered heterocyclic ring which itself may be substituted or unsubstituted. Preferably, X is either a carbon atom or a nitrogen atom, for example, as part of a ==C(NHQ)- group where Q is a hydrogen atom, a substituted or unsubstituted alkyl group, an amino group or a hydroxy group; as part of an >C=O group; as part of an >NH group; or as part of an ==N— group.

Y in the above structural formula forms, with X, a nitrogen-containing, five- or six-membered heterocyclic ring which itself may be substituted or unsubstituted. Preferably, Y is a carbon atom or a nitrogen atom, for example, as part of a —CH$_2$—; >C=O; >C=S; ==C(NHQ)- where Q is a hydrogen atom, a substituted or unsubstituted alkyl group, amino group or a hydroxy group; ==C(CH$_3$)—; ——N==; or >NH. More preferably, Y is a part of a —CH$_2$—, >C=O, >C=S, ==C(NH$_2$)—, or ==C(CH$_3$)— group. Most preferably, Y is a ==C(NH$_2$)— group.

Together, X and Y form a nitrogen-containing, 5- or 6-membered heterocyclic ring which may be substituted or unsubstituted. Examples of such heterocyclic rings include, for example, pyrrole, 2H-pyrrole, imidazole, pyrazole, pyridine, pyrazine, pyrimidine, pyridazine, isothiazole, isoxazole or furazan rings. Preferably, the heterocyclic formed by X and Y taken together is selected from the group consisting of:

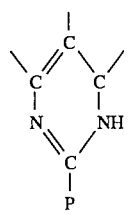

wherein P is a hydrogen atom, a substituted or unsubstituted alkyl group or an amino group;

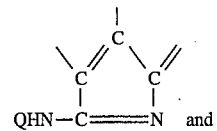

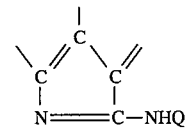

wherein Q is a hydrogen atom, a substituted or unsubstituted alkyl group, or an amino or hydroxy group;

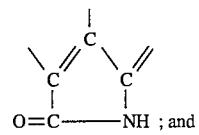

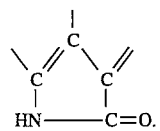

In a particularly preferred embodiment according to the present invention, Z is a nitrogen atom; W is an unsubstituted alkylene group; Ar is a monocyclic or bicyclic, substituted or unsubstituted aryl or heteroaryl ring; R$^1$ is a hydrogen atom; A is a hydrogen, halogen or carbon atom; and X is a nitrogen atom. Even more preferred substituted naphthalene ring compounds are those wherein W is a methylene group; A is a hydrogen atom; X is a nitrogen atom which, taken together with a hydrogen atom, forms an —NH== group; and Y is a carbon atom. The most preferred substituted naphthalene ring compounds in this first embodiment are those falling within the above parameters and wherein, additionally, R is methyl, Ar is a 4-phenylsulfonyl group, and Y is a carbon atom substituted with an amino group to form a ==C(NH$_2$)— group.

In a second embodiment of the invention, preferred substituted naphthalene compounds according to the present invention are those wherein Z is a nitrogen atom; W is an unsubstituted alkylene group; Ar is a phenyl group substituted with an electron withdrawing moiety; R$^1$ is a hydrogen atom; A is a hydrogen, halogen or carbon atom; R is selected from the group consisting of methyl, ethyl, hydroxyethyl, n-propyl, isopropyl, hydroxypropyl, and —CH$_2$—S—CH$_3$; and X and Y are independently a carbon atom or a nitrogen atom. In this second embodiment, even more preferred compounds are those wherein W is a methylene group; the electron withdrawing moiety is a >C=O or a >SO$_2$ group directly bonded to an amino acid group, a substituted or unsubstituted aryl group, a substituted or unsubstituted alkyl group, or a substituted or unsubstituted heterocyclic group; and A is a hydrogen atom or a carbon atom.

In this second embodiment, X and Y together may form a substituted or unsubstituted heterocyclic ring containing two nitrogen atoms. Preferably, Ar is a phenyl group substituted in the para position with a >SO$_2$ group directly bonded to a second phenyl group; A is a hydrogen atom; X is a nitrogen atom; Y is a nitrogen atom; and X and Y together form a heterocyclic ring having the formula:

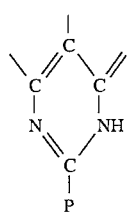

wherein P is a hydrogen atom, a substituted or unsubstituted alkyl group, or an amino group. Most preferably, P is methyl group.

Alternatively, in the above preferred group of compounds, A is a carbon atom which forms a portion of a substituted or unsubstituted alkyl group. Then, preferably, A is a carbon atom which, taken together with three hydrogen atoms, forms a methyl group.

A second group of compounds in this second embodiment include those substituted naphthalene ring compounds wherein X and Y together form a substituted or unsubstituted heterocyclic ring containing one nitrogen atom. Preferably, Ar is a phenyl group substituted in the para position with a $>SO_2$ group directly bonded to a second phenyl group; A is a hydrogen atom, a halogen atom, or a carbon atom which, when taken together with other atoms, forms a substituted or unsubstituted alkyl group; X is a nitrogen atom; Y is a carbon atom; and X and Y together form a heterocyclic ring having the formula:

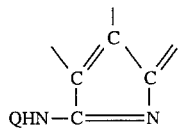

wherein Q is a hydrogen atom, a substituted or unsubstituted alkyl group, or an amino or hydroxy group. Most preferably, A is a hydrogen atom, a chlorine atom, or a carbon atom which, taken together with three hydrogen atoms, forms a methyl group; and Q is a hydrogen atom, or a methyl or hydroxy group.

Alternatively, X is a carbon atom; Y is a nitrogen atom; and X and Y together may form a heterocyclic ring having the formula:

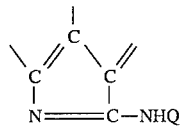

wherein Q is a hydrogen atom, a substituted or unsubstituted alkyl group, or an amino or hydroxy group. Then, most preferably, A is a hydrogen atom and Q is a hydrogen atom.

Further still, X and Y together may form a heterocyclic ring having the formula:

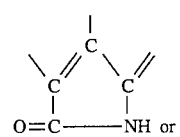

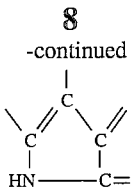

Then, most preferably, A is a hydrogen atom or a carbon atom which, taken together with three hydrogen atoms, forms a methyl group.

In a third embodiment of the present invention, Ar is substituted with an electron withdrawing $>C=O$ or a $>SO_2$ group directly bonded to a substituted or unsubstituted heterocyclic ring. The heterocyclic ring is preferably selected from the group consisting of pyrimidines, pyrrolidines, pyrroles, and indoles.

Even more preferably, with this group of preferred compounds, A is a hydrogen atom, a halogen atom, or a carbon atom which, when taken together with other atoms, forms a substituted or unsubstituted alkyl group; X is a nitrogen atom; Y is a carbon atom; and X and Y together form a heterocyclic ring having the formula:

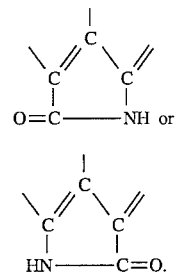

wherein Q is a hydrogen atom, a substituted or unsubstituted alkyl group, or an amino or hydroxy group. Most preferably, A is a hydrogen, chlorine or carbon atom which, taken together with three hydrogen atoms, forms a methyl group; and Q is a methyl or hydroxy group.

Examples of useful compounds of the invention include those found in Table I relating to the working examples provided by this document and the following additional specific examples:

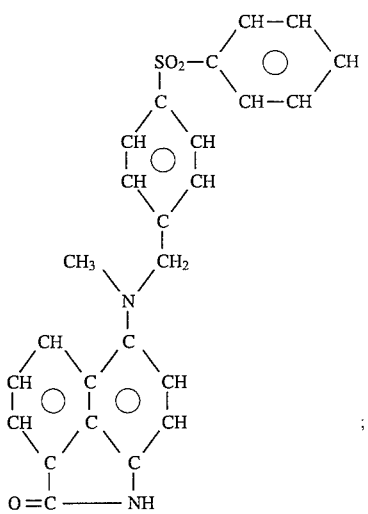

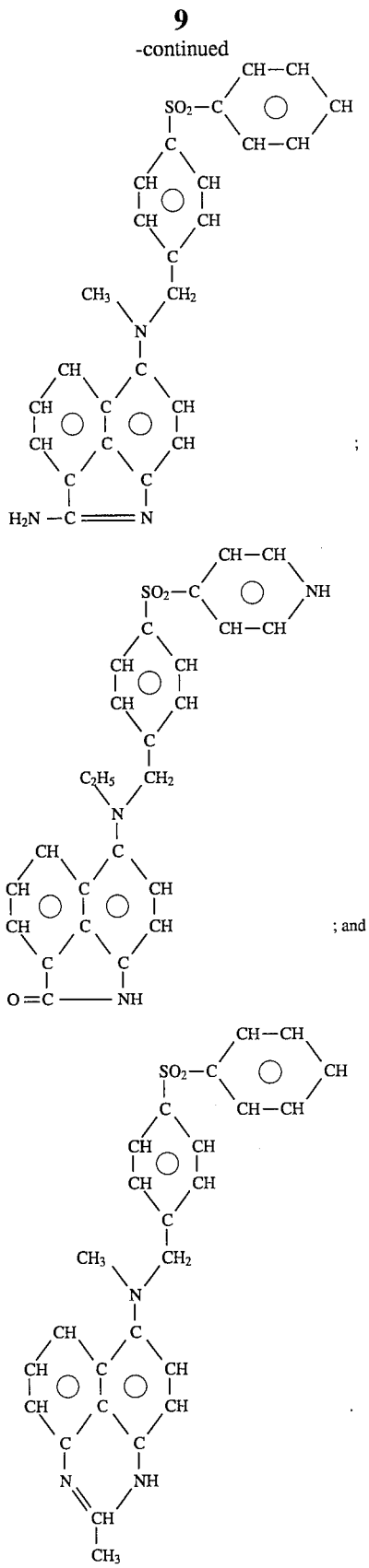

; and

The invention also relates to a process for making the compounds of the present invention wherein Z is a nitrogen atom by successive alkylation of an aniline having the formula:

wherein A, X and Y are as defined above. The successive alkylation is carried out by reacting the above aniline with an activated group R-Act, wherein R is as defined above and Act is an activating group which is preferably selected from the group consisting of halogen such as bromo, chloro or iodo, sulfonate, aromatic or alkyl aldehyde, and the like. Halogen is a particularly preferred activating group. The alkylation preferably takes place in a suitable organic solvent, such as tetrahydrofuran, dioxane, 1,2-dimethoxyethane, dimethylformamide, dimethylacetamide, or the like. Especially preferred solvents include dimethylformamide and dimethylacetamide.

The first alkylation step preferably also takes place in the presence of an organic or inorganic weak base, for example, a substituted amine such as trimethylamine, triethylamine, diisopropylethylamine, dimethyl-sec-butylamine, N-methyl-N-ethylaniline, N,N-dimethylaniline, diazobicyclicundecine, tributylamine or the like; or an inorganic carbonate, such as sodium, potassium and/or calcium carbonate; and the like.

The temperature of the first alkylation step varies widely, but, typically, is in the range from about 65° C. to about 130° C. The time required for the reaction will depend to a large extent on the temperature used and the relative reactivities of the starting material but, typically, varies from about 1 to 20 hours.

The product of the first alkylation step is then typically reacted under similar conditions with the compound Act-W-Ar where Act, W and Ar are as defined above to form a second alkylated compound.

It should be noted that one or more of -R and -Ar may contain a chemical group or groups which, either before, after or during the course of either the first alkylation step (1) or the second alkylation step (2):

(a) may be protected by a protecting group or (b) may have one or more of any protecting groups present removed.

A suitable protecting group for a ring nitrogen, such as may be included in Ar, is for example, a pivaloyloxymethyl group, which may be removed by hydrolysis with a base such as sodium hydroxide; a tert-butyloxycarbonyl group, which may be removed by hydrolysis with an acid, such as hydrochloric acid or trifluoroacetic acid, or with a base such as tetra-n-butylammonium fluroide ("TBAF") or lithium hydroxide; or a 2-(trimethylsilyl)ethoxymethyl group, which may be removed by TBAF or with an acid such as hydrochloric acid.

A suitable protecting group for a hydroxyl group is, for example, an esterifying group such as an acetyl or benzoyl group, which may be removed by hydrolysis with a base such as sodium hydroxide. Alternatively, when other groups present in the starting material do not contain an alkenyl or alkynyl group, the protecting group may be, for example, an alpha-arylalkyl group such as a benzyl group, which may be removed by hydrogenation in the presence of a catalyst such as palladium on charcoal or Raney nickel. An additional protective group for a hydroxyl group is a group such as t-butyldiphenylsilyl (—Si-t-Bu—Ph$_2$), which may be removed by treatment with TBAF.

A suitable protective group for a mercapto group is, for example, an esterifying group such as an acetyl group, which may be removed by hydrolysis with a base such as sodium hydroxide.

A suitable protective group for an amino group may be, for example, an alkylcarbonyl group such as an acetyl group (CH$_3$CO—), which may be removed by treatment with hydrogen gas in the presence of a reduction catalyst or by treatment with an inorganic acid such as nitric, sulfuric or hydrochloric acid. Another protective group for an amino group is an alkoxycarbonyl group such as a methoxycarbonyl or a tert-butyloxycarbonyl group. These groups may be removed by treatment with an organic acid such as trifluoroacetic acid.

A suitable protective group for a primary amino group is, for example, an acetyl group, which may be removed by treatment with an inorganic acid such as nitric, sulfuric, or hydrochloric acid, or a phthaloyl group, which may be removed by treatment with an alkylamine such as dimethylaminopropyl amine or with hydrazine.

A suitable protective group for a carboxy group may be an esterifying group, for example, a methyl or an ethyl group, which may be removed by hydrolysis with a base such as sodium hydroxide. Another useful protecting group is a tert-butyl group, which may be removed by treatment with an organic acid such as trifluoroacetic acid.

Preferred protective groups include an esterifying group, an alpha-arylalkyl group, an alkylcarboxyl group, a substituted or unsubstituted alkoxycarbonyl group, a phthaloyl group, a pivaloyloxymethyl group, a methyl oxyether-type group such as methoxymethyl or 2-(trimethylsilyl)ethoxymethyl, or a silicon group such as a tert-butyldiphenylsilyl group.

A particular aspect of the invention relates to a process of making a naphthalene ring compound capable of inhibiting thymidylate synthase having the formula:

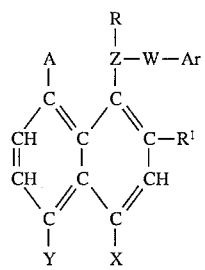

wherein Z, W, Ar, R, R$^1$, A are as defined above for the compounds of the invention, and where X and Y together form a heterocyclic ring having one of the following formulas:

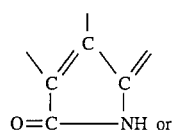 (A)

or

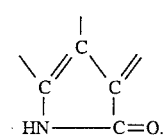 (B)

It should also be noted that, when X and Y form a ring of formula (A), the substituent A is not an election-withdrawing group. In any event, A is preferably a carbon atom which, taken together with other atoms, forms a substituted or unsubstituted alkyl group. Most preferably, A is a carbon atom which, taken with three hydrogen atoms, forms a methyl group.

A process of making this group of substituted naphthalene compounds may comprise the steps of:

(1) treating a compound having the formula (Ia) or (IIa):

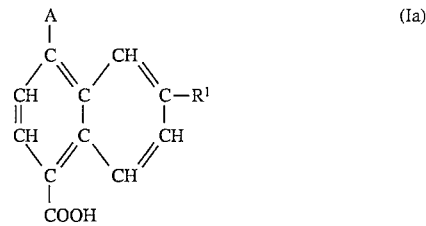 (Ia)

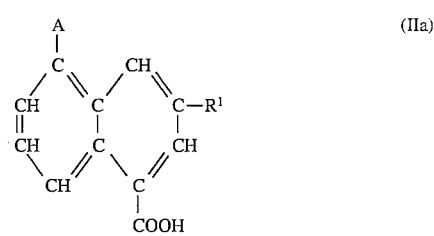 (IIa)

wherein R$^1$ and A are as defined above, with a lower alkyl haloformate and a base in a first solvent to form an activated acid derivative;

(2) treating the activated acid derivative with sodium azide at a temperature below room temperature to form a naphthylacylazide;

(3) heating the naphthylacylazide in a second solvent to form an isocyanate; and (4) treating the isocyanate with a Lewis acid to form a compound having a formula (I) or (II):

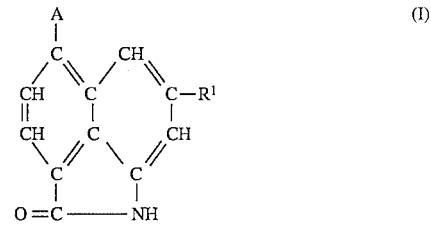 (I)

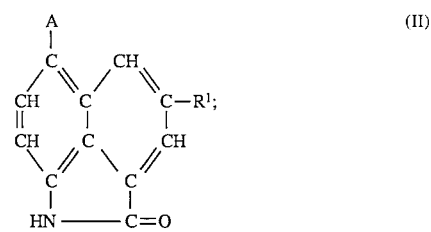 (II)

(5) reacting a compound derived from the compound of formula (I) or formula (II) with the compound R-Act wherein R-Act is defined as above to form a first alkylated compound; and (6) reacting the first alkylated compound with the compound Act-W-Ar where Act, W and Ar are as defined above to form a second alkylated compound.

The term "activated acid derivative" refers to derivatives of acid compounds such as acid chlorides, carbonates, imidazolides, mixed phosphate and carbon type anhydrides and other known acid derivatives.

In the first step, treating a compound of formula (Ia) or (IIa) with a lower alkyl haloformate and a base in a first solvent, the lower alkyl haloformate may be ethyl chloroformate, benzyl chloroformate, methyl chloroformate or the like, but is preferably ethyl chloroformate. The first solvent may be any suitable organic solvent such as tetrahydrofuran, dioxane, dichloromethane, benzene, acetone, toluene and the like, but is preferably acetone. The temperature at which the first step takes place may vary widely from just above room temperature to about −78° C., but preferably takes place at temperatures well below room temperature such as about −5° C. The activated acid derivative produced during this first step is typically used directly in the following step without isolating the product or otherwise removing the first solvent.

The second step of treating the activated acid derivative produced in the first step with sodium azide at a temperature below room temperature can be carried out at a temperature ranging from about −78° to about 25° C., is preferably carried out a temperature ranging from about −20° to about 10° C., most preferably at about −5° C. If the activated acid derivative produced in the first step has been used directly without attempting to isolate the acid chloride product, the solvent used in the second step will be, of course, whatever first solvent was used in the first step. If the activated acid derivative produced as a result of the first step was isolated, or if the first solvent was otherwise removed, further amounts of the first solvent or some other like solvent, such as tetrahydrofuran, dioxane, dichloromethane, benzene, acetone, toluene and the like are typically used in the second step.

The third step, heating the naphthylacylazide formed as a result of the second step to form an isocyanate, can be carried out at nearly any temperature up to about 240° C. The temperature, however, typically varies from about 50° to about 160° C., from about 80° to about 140° C. and, most preferably, is about about 135° C. Preferably, the temperature is maintained at the boiling point of the second solvent in which the reaction takes place. The second solvent should also be completely anhydrous (i.e., contain less than about 0.1% water) and should not react with either the naphthylazide starting material or the isocyanate product of the reaction. Preferred solvents include such solvents as nitrobenzene, methylene chloride, chlorobenzene, dichloroethane and mixtures thereof. Most preferably, the second solvent is chlorobenzene, nitrobenzene or a mixture thereof. Preferably, also, the third step is carried out in a dry, inert atmosphere, such as under a nitrogen, argon or helium atmosphere. Most preferably, the third step is carried out under a nitrogen or an argon atmosphere.

The fourth step involves treating the isocyanate formed as a result of the third step with a Lewis acid to form a compound of formula (I) or (II). The Lewis acid used in the fourth step is typically one selected from the group consisting of boron trichloride, aluminum chloride, boron trifluoride etherate, titanium tetrachloride, and tin tetrachloride. Preferably, the Lewis acid is boron trichloride. The fourth step can take place in the presence of an organic solvent such as chlorobenzene, dichlorobenzene, nitrobenzene, dichloroethane, or a mixture thereof.

Step (5), a first alkylating step, involves reacting a compound derived from the compound of formula (I) or formula (II) with the compound R-Act, and Step (6), a second alkylating step, involves reacting the product of the first alkylation step with Ar-W-Act to form a second alkylated compound, as described above in detail. Steps (5) and (6) can also be done in reverse order.

In one preferred embodiment, the resulting second alkylated compound is treated with either $P_2S_5$ or with Lawsen's Reagent (2,4-bis(4-methoxyphenyl)-1,3-dithia-2,4-diphosphetane-2,4-disulfide) to form a corresponding thiono compound, as follows:

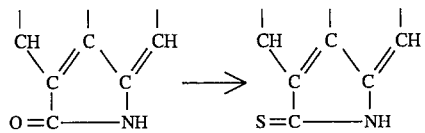

The resulting thiono compound may then be reacted with an alkyl halide to form a corresponding alkylated thiolactam, for example, by the reaction below:

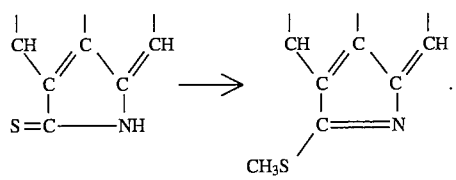

The corresponding alkylated thiolactam may itself then be treated with any one of a number of nucleophiles, such as ammonia, alkyl amines, alkoxyamines, hydroxylamines and hydrazines, to form the corresponding amidine, alkylated amidine, hydroxylated amidine and aminated amidine rings.

Another aspect of the invention relates to processes of making a substituted naphthalene compound of the following formula,

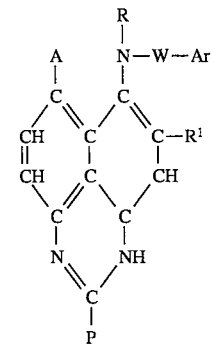

wherein W, Ar, R, $R^1$, A and P are as defined above for the compounds of the invention, and where X and Y have formed a perimidine ring. A preferred process of making this group of naphthalene compounds comprises the steps of:

(1) reacting a compound R-Z-W-Ar with a starting naphthalene compound of the formula:

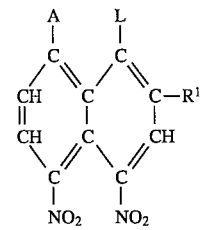

where L is a leaving group, for example, a halogen atom such as F or Cl, to form the following intermediate having two nitro groups:

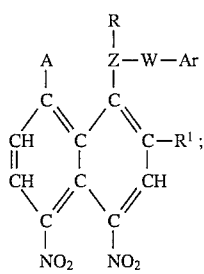

(2) reducing the two nitro groups of the intermediate to form the corresponding amino groups; and (3) cyclizing the resulting amino groups to form the desired substituted naphthalene compound of the invention where X and Y have formed a perimidine ring.

The first step of reacting the compound R-Z-W-Ar with a starting naphthalene compound can be carried out under widely varying conditions but is typically carried out in the presence of an organic solvent, such as dimethylsulfoxide, dioxane or dimethoxy ethane, in the presence of a neutralizing agent such as calcium carbonate, sodium carbonate, potassium carbonate, cesium carbonate or a trisubstituted amine, and at a temperature varying widely from room temperature to about 180° C., preferably from about 100° to about 150° C., most preferably at about 130° C.

The second step, the reducing step, can be performed under widely varying reduction conditions, but is preferably carried out in water or in an organic solvent such as ethanol, methanol, ethyl acetate, tetrahydrofuran or acetic acid, in the presence of a reducing agent such as a hydrazine compound, hydrogen gas under a vapor pressure of one atmosphere or higher. Preferably, a reduction catalyst is also used, such as Raney nickel, palladium on charcoal, palladium on barium sulfate or the like.

In the third step, the cyclization step, the reagent used to induce cyclization will determine identity of the substituent, P, on the perimidine ring of the resulting substituted naphthalene compound of the invention. The cyclization reagent can, for example, be a wide variety of compounds such as acetic anhydride, trimethylorthoformate, triethylorthoformate, or cyanogen bromide but, typically, is an organic anhydride compound such as acetic anhydride. When the cyclization reagent used is, for example, acetic anhydride, P on the resulting perimidine ring is a methyl group. If, on the other hand, a cyclization reagent such as cyanogen bromide is used, P would be an amino group.

Another aspect of the invention relates to a pharmaceutical composition comprising a pharmaceutically acceptable diluent or carrier in combination with at least one compound according to the present invention in an amount effective to inhibit thymidylate synthase. The composition preferably contains a compound of the invention in a total amount which is suitable for therapeutic effect.

The substituted naphthalene compounds of the present invention which may be employed in the pharmaceutical compositions of the invention include all of those compounds described above, as well as the pharmaceutically acceptable salts of these compounds. Pharmaceutically acceptable acid addition salts of the compounds of the invention containing a basic group are formed where appropriate with strong or moderately strong organic or inorganic acids in the presence of a basic amine by methods known to the art. Exemplary of the acid addition salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts. Pharmaceutically acceptable base addition salts of compounds of the invention containing an acidic group are prepared by known methods from organic and inorganic bases and include nontoxic alkali metal and alkaline earth bases, for example, calcium, sodium, and potassium hydroxide; ammonium hydroxide, and nontoxic organic bases such as triethylamine, butylamine, piperazine, and tri(hydroxymethyl)methylamine.

As stated above, the compounds of the invention possess antiproliferative activity, a property which may express itself in the form of antitumor activity. A compound of the invention may be active per se or it may be a pro-drug that is converted in vivo to an active compound. Preferred compounds of the invention are active in inhibiting the growth of the L1210 cell line, a mouse leukemia cell line which can be grown in tissue culture. Such compounds of the invention are also active in inhibiting the growth of bacteria such as $E.Coli$, a gram-negative bacterium which can be grown in culture.

The substituted naphthalene compounds according to the present invention, as well as the pharmaceutically acceptable salts thereof, may be incorporated into convenient dosage forms such as capsules, tablets, or injectable preparations. Solid or liquid pharmaceutically acceptable carriers may be employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g. solution), such as an ampoule, or an aqueous or nonaqueous liquid suspension.

The pharmaceutical preparations are made following conventional techniques of a pharmaceutical chemist involving steps such as mixing, granulating, and compressing, when necessary, for tablet forms, or mixing, filling and dissolving the ingredients, as appropriate, to give the desired products for oral, parenteral, topical, intravaginal, intranasal, intrabronchial, intraocular, intraaural and rectal administration.

The compositions of the invention may further comprise one or more other compounds which are antitumor agents, such as mitotic inhibitors (e.g., vinblastine), alkylating agents (e.g., cisplatin, carboplatin and cyclophosphamide), DHFR inhibitors (e.g., methotrexate, piritrexim or trimetrexate), antimetabolites (e.g., 5-fluorouracil and cytosine arabinoside), intercalating antibiotics (e.g., adriamycin and bleomycin), enzymes (e.g., asparaginase), topoisomerase inhibitors (e.g., etoposide) or biological response modifiers (e.g., interferon).

The composition of the invention may also comprise one or more other compounds including antibacterial, antifungal, antiparasitic, antiviral, antipsoriatic and anticoccidial agents. Exemplary antibacterial agents include, for example, sulfonamides such as sulfamethoxazole, sulfadiazine, sulfameter or sulfadoxine; DHFR inhibitors such as trimethoprim, bromodiaprim, or trimetrexate; pencillins; cephalosporins; aminoglycosides; bacteriostatic inhibitors of protein synthesis; the quinolonecarboxylic acids and their fused isothiazolo analogs.

Another aspect of the invention relates to a therapeutic process of inhibiting thymidylate synthase which process comprises administering to a vertebrate host, such as a mammal or bird, an amount effective to inhibit thymidylate synthase of a naphthalene compound according to the present invention. The compounds of the invention are particularly useful in the treatment of mammalian hosts, such as human hosts, and in the treatment of avian hosts.

Any of the substituted naphthalene compounds described above, or pharmaceutically acceptable salts thereof, may be employed in the therapeutic process of the invention. The compounds of the invention may be administered in the therapeutic process of the invention in the form of a pharmaceutically acceptable composition comprising a diluent or carrier, such as those described above. Doses of the compounds preferably include pharmaceutical dosage units comprising an efficacious quantity of active compound. By an efficacious quantity is meant a quantity sufficient to inhibit TS and derive the beneficial effects therefrom through administration of one or more of the pharmaceutical dosage units. An exemplary daily dosage unit for a vertebrate comprises an amount of up to about 5,000 mg of active compound per square meter of the body area of the vertebrate host.

The selected dose may be administered to a warm-blooded animal or mammal, for example a human patient, in need of treatment mediated by thymidylate synthase inhibition by any known method of administration, including topically (e.g. as an ointment or cream), orally, rectally (e.g., as a suppository), parenterally, by injection, or continuously by infusion, intravaginally, intranasally, intrabronchially, intra-aurally or intraocularly.

The substituted naphthalene compounds according to the present invention may be further characterized as producing any one or more of an antiproliferative effect, an antibacterial effect, an antiparasitic effect, an antiviral effect, an antipsoriatic effect, an antiprotozoal effect, an anticoccidial effect or an antifungal effect. The compounds are especially useful in producing an antitumor effect in a vertebrate host harboring a tumor.

The compounds of the present invention are antagonists of a folate cofactor and therefore may affect one or more other folate-dependent enzymatic systems as well. Examples of other folate-dependant enzymatic systems which may be affected include 5,10-methylenetetrahydrofolate reductase, serine hydroxymethyltransferase, and glycineamineribotide transformylase.

The following examples illustrate the invention, although the scope and spirit of the invention are not limited thereto.

EXAMPLES

The structures of all compounds of the invention were confirmed by proton magnetic resonance spectroscopy, infrared spectroscopy, elemental microanalysis and, in certain cases, by mass spectrometry.

Proton magnetic resonance spectra were determined using a General Electric QE-300 spectrometer operating at a field strength of 300 MHz. Chemical shifts are reported in parts per million (d) and by setting the references such that, in $CDCl_3$, the $CHCl_3$ peak is at 7.26 ppm and, in $D_6DMSO$, the DMSO peak is at 2.49 ppm. Standard and peak multiplicities are designated as follows: s, singlet; d, doublet; dd, doublet of doublets; t, triplet; brs, broad singlet; brd, broad doublet; br, broad signal; m, multiplet.

Mass spectra were determined using a VG 7070E-HF high resolution mass spectrometer using the direct insertion method, an ionizing voltage of 70 eV, and an ion source temperature of 200° C. Infrared absorption spectra were taken on a Perkin-Elmer 457 spectrometer. Elemental microanalysis gave results for the elements stated with ±0.4% of the theoretical values.

General procedures were as follows:

N-N-Dimethylformamide ("DMF") was dried over activated (250°) 3-Å molecular sieves; N,N-dimethylacetamide ("DMA") (Aldrich Gold Label grade) was similarly dried. Tetrahydrofuran ("THF") was distilled from sodium benzophenone ketyl under nitrogen. The term "ether" refers to diethyl ether.

Flash chromatography was performed using Silica gel 60 (Merck Art 9385). Where the crude solid was insoluble in the chosen eluant, it was dissolved in a more polar solvent and Merck Art 7734 silica was added. The slurry was evaporated to dryness on a rotary evaporator fitted with a coarse glass frit to prevent spraying of the silica. The coated silica was then applied to the column. Thin layer chromatographs ("TLC") were performed on precoated sheets of silica 60 $F_{254}$ (Merck Art 5719). Extracts were dried over anhydrous $Na_2SO_4$ or $MgSO_4$. Melting points were determined on a Mel-Temp apparatus and are uncorrected.

Example 1

Preparation of Compounds 1 through 6

Compounds 1 through 6 were prepared according to the following reaction scheme:

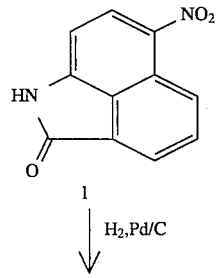

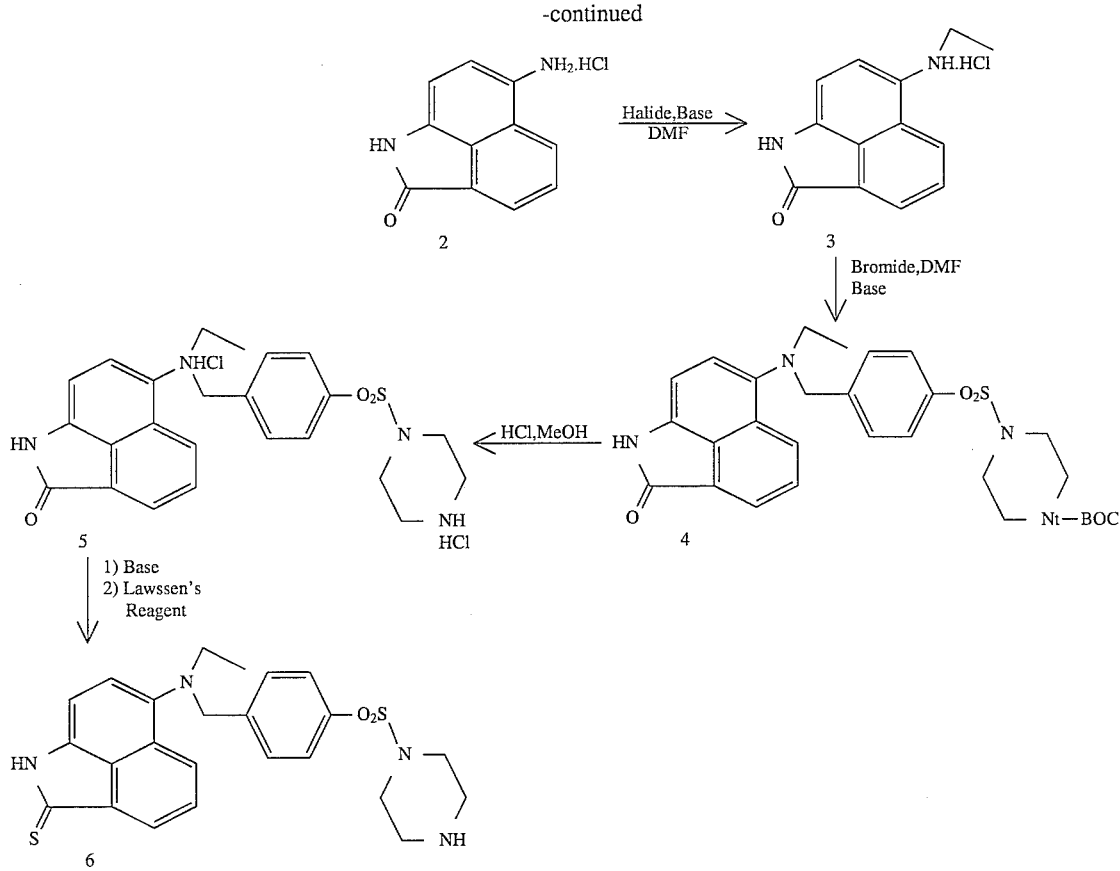

Preparation of Compound 1—6-Nitrobenz[cd]indol-2(1H)-one

To a mixture of 33.9 g (0.200 mol) benz[cd]indol-2(1H)-one in 150 ml glacial acetic acid was added dropwise 16.5 ml (0.260 mol) nitric acid. At first, there was a very minor exotherm and then, over the course of one hour, the reaction temperature rose to 50° C. The reaction mixture was gradually cooled to room temperature with a cold water bath. A thick dark green paste resulted. This mixture was filtered, washed with 50% aqueous acetic acid, and pulled as dry as possible. The resulting wet filter cake was refluxed in 600 ml methanol and then cooled to 0° C. The mixture was filtered, washed with cold methanol and dried in vacuo to yield 22.2 g (51% theory) of 6-nitrobenz[cd]indol-2(1H)-one. TLC (CHCl$_3$:MeOH 95:5) showed the product to be essentially one spot material.

An analytically pure sample was obtained by refluxing 10.52 g of 6-nitrobenz[cd]-indol-2(1H)-one in 350 ml THF. After refluxing for 30 minutes, the mix was filtered, and the filtrate was vaporated to near dryness. The resulting wet solid was stirred in 200 ml methanol and then evaporated to near dryness. The methanol slurry and evaporation was repeated. Finally, the wet cake was taken up in 200 ml methanol, heated to reflux, and cooled at −4° C. overnight. The mixture was filtered, and then the filter cake was washed with cold methanol and dried in vacuo to yield 8.97 g (85% theory) of an orange solid: m.p. 298°–300° C. (lit. 297°–298° C.); $^1$H NMR (d$_6$-DMSO TMS) δ (ppm): 7.10 (d,1H,J=9 Hz), 8.05 (dd,1H,J=6 Hz), 8.16 (d,1H,J=6 Hz), 8.61 (d,1H,J=6 Hz), and 8.85 (d,1H,J=9 Hz).

Preparation of Compound 2—6-Aminobenz[cd]indol-2(1H)-one Hydrochloride

A solution of 4.00 g (18.7 mmol) 6-nitrobenz[cd]indol-2(1H)-one(1) in 300 ml THF was filtered into a Parr hydrogenation bottle. The insolubles were discarded. To the solution in the Parr bottle was added 0.44 g 5% Pd/C (i.e., palladium on charcoal). This mix was hydrogenated at 40 psi H$_2$ on the Parr hydrogenator overnight with agitation. The next morning, the H$_2$ pressure had dropped to 37 psi. The Parr bottle was vented, the reaction mixture was filtered through a diatomaceous earth material commercially available under the trade name "Celite", and the filtrate was evaporated. The residue was taken up in hot ethanol, filtered, and then acidified with ethanol saturated with HCl (g). A precipitate formed. 500 ml of diethyl ether was added dropwise to the mix. The mix was filtered, and the resulting filter cake was washed with diethyl ether and dried in vacuo, yielding 3.44 g of reddish solid. This material was refluxed in 150 ml ethanol and cooled, and then 500 ml diethyl ether was added dropwise. The resulting precipitate was collected, washed with diethyl ether, and dried in vacuo to yield 3.16 g (77% theory) 6-aminobenz[cd]indol-2(1H)-one hydrochloride. TLC (CHCl$_3$:MeOH:HoAc 19:5:1) showed the material to be pure.

A sample of the free base was prepared by dissolving 1.51 g of the hydrochloride salt in 200 ml water and basifying the solution with saturated aqueous bicarbonate solution. The precipitate formed was collected, washed with water, and dried in vacuo to yield 1.21 g 6-aminobenz[cd]indol-2(1H)-one: m.p. 240°–242° C. (lit. 244° C.); $^1$H NMR (D$_6$-Acetone/TMS) δ (ppm): 2.85 (bs,2H), 5.21 (bs,1H), 6.64 (d,1H,J=9 Hz), 6.76 (d,1H,J=9 Hz), 7.71 (dd,1H,J=6 Hz), 7.87 (d,1H,J=6 Hz), and 8.22 (d,1H,J=6 HZ).

Preparation of Compound 3—N⁶-Ethyl-6-Aminobenz[cd]indol-2(1H)-one Hydrochloride To a mixture of 3.26 g (0.0148 mol) 6-aminobenz[cd]indol-2(1H)-one hydrochloride (2), 4.18 g (0.0303 mol) anhydrous potassium carbonate, and 60 ml DMF was added 1.77 ml (0.0222 mol) ethyl iodide. This mixture was heated at 70°–100° C. for eight hours then cooled to room temperature, diluted with ethyl acetate, filtered, and evaporated to dryness. The resulting residue was taken up in a solution of chloroform:methanol 9:1 and chromatographed on flash grade silica using chloroform:methanol 9:1 as elutant. Fractions that contained only pure product were combined and evaporated, yielding 2.63 g of crude product. This material was taken up in ethyl acetate/methanol and acidified with ethyl acetate saturated with HCl (g). To this mixture was added dropwise sufficient diethyl ether to precipitate the product. The precipitate was collected, washed with diethyl ether and dried in vacuo to yield 2.25 g (61% theory) N⁶-ethyl-6-aminobenz[cd]indol-2(1H)-one hydrochloride: m.p. 261.5°–263° C.

| Analysis | Theory | Found |
|---|---|---|
| C | 62.78 | 62.63 |
| H | 5.27 | 5.44 |
| N | 11.26 | 11.23 |
| Cl | 14.25 | 14.00 |

¹H NMR (d₆-DMSO/TMS) δ (ppm): 1.30 (t,3H,J=6 Hz), 3.36 (q,2H,J=6 Hz), 4.0 (bs,2H), 6.98 (d,1H,J=9 Hz), 7.35 (bs,1H), 7.87 (t,1H,J=6.9 Hz), 8.08 (d,1H,J=6 Hz), 8.51 (d,1H,J=9 Hz), and 10.86 (s,1H).

Preparation of Compound 4—N⁶-Ethyl-N6-[4-(N,N-1-t-butoxycarbonyl)piperazinyl)sulfamoly]benzyl-6-aminobenz[cd]indol-2(1H)-one A mixture of 0.371 g 4-bromomethyl [N,N-(t-butoxycarbonyl)piperazinyl]benzenesulfanomide (12) (~70% pure, 0.619 mmol), 0.171 g (1.24 mmol) anhydrous potassium carbonate, 0.154 g (0.619 mol) N⁶-ethyl-6aminobenz[cd]indol-2(1H)-one hydrochloride, and 20 ml DMF were heated at 100° C. until TLC (ethyl acetate) of an aliquot showed no further consumption of starting material. The reaction mixture was cooled to room temperature and added to 100 ml water. A small amount of saturated aqueous sodium chloride solution was added to coagulate the solid. The precipitate was collected by filtrating, washed with water, and dried in vacuo, yielding 0.37 g of impure product. This material was dissolved in chloroform and purified by chromatography on flash grade silica using ethyl acetate:hexene 1:1 as the elutant. Fractions containing pure product were combined and evaporated to yield 0.16 g (47% theory) of a pure glass. ¹H NMR (CDCl₃/TMS) δ (ppm): 1.12 (t,3H,J=9 Hz), 1.40 (S,9H), 2.95 (m,4H), 3.25 (q,2H,J=9 Hz), 3.50 (m,4H), 4.43 (S,2H), 6.84 (d,1H,J=9 Hz), 6.92 (d,1H,J=9 Hz), 7.54 (d,2H,J=9 Hz), 7.67 (d,2H,J=9 Hz), 7.75 (dd,1H,J=9 Hz), 8.09 (d,1H,J=9 Hz), and 8.30 (m,2H).

Preparation of Compound 5—N⁶-[4-(N,N-Piperazinyl)sulfamoyl]benzyl-6-aminobenz[cd]indol-2(1H)-one A solution of 0.161 g (0.292 mmol) N⁶-ethyl-N⁶-[4-(N,N-(1-t-butoxycarbonyl)piperazinyl)sulfamoyl]benzyl-6-aminobenz[cd]indol-2(1H)-one (4) in 10 ml MeOH was acidified with methanol saturated with HCl (g). This solution was stirred at room temperature until TLC (ethyl acetate) showed all starting material had been consumed. The solvent was evaporated and the residue partitioned between saturated aqueous sodium bicarbonate solution and chloroform. The chloroform solution of product was evaporated, and the residue was taken up in fresh chloroform and purified by chromatography on flash grade silica using chloroform:methanol 95:5 as the elutant. Fractions containing pure product were combined and evaporated to yield 0.124 g of a yellow solid (94% theoretical yield); ¹H NMR (CDCl₃/TMS) δ (ppm): 1.11 (t,3H,J=9 Hz), 2.93 (m,8H), 3.24 (q,2H,J=9 Hz), 4.42 (s,2H), 6.86 (d,1H,J=9 Hz), 6.94 (d,1H,J=9 Hz), 7.55 (d,2H,J=9 Hz), 7.67 (d,2H,J=9 Hz), 7.73 (dd,1H,J=6 Hz), 8.09 (d,1H,J=6 Hz), 8.29 (d,1H,J=6 Hz), and 8.56 (s,1H).

For analytical purposes, 102 mg of the free base was taken up in 5 ml ethyl acetate and acidified with ethyl acetate saturated with HCl (g). Diethyl ether was added to precipitate the product. The yellow solid was collected by filtration, washed with diethyl ether, and dried in vacuo to yield 92 mg of hydrochloride salt.

| Analyzed | Theory | Found |
|---|---|---|
| C | 55.07 | 54.93 |
| H | 5.39 | 5.43 |
| N | 10.75 | 10.58 |
| S | 6.13 | 5.95 |
| Cl | 13.54 | 13.61 |

Preparation of Compound 6—N-⁶-Ethyl-N⁶[(4-N,N-piperazinyl)sulfamoyl]benzyl-6-aminobenz[cd]indol-2(1H)-thione A mixture of 0.124 g (0.275 mmol) N⁶-ethyl-N⁶-[4-(N,N-piperazinyl)sulfamoyl]benzyl-6-aminobenz[cd]indol-2(1H)-one (5), 0.061 g (0.151 mmol) Lawsson's reagent (i.e., 2,4-bis(4-methoxyphenyl)-1,3-dithia-2,4-diphosphetane-2,4-disulfide), and 10 ml toluene was refluxed for one hour. The solvent was evaporated. The residue was dissolved in chloroform and purified by chromatography on flash grade silica using chloroform:methanol 95:5 as the elutant. Fractions containing pure product were combined and evaporated yielding 0.100 g (78% theory) of a purple solid. Exact mass spectrometry requires 466.1498. Found: 466.1518. ¹H NMR (CDCl₃/TMS) δ (ppm) 1.15 (t,3H,J=6 Hz), 2.96 (m,8H), 3.29 (q,2H,J=6 Hz), 4.48 (s,2H), 6.88 (d,1H J=9 Hz), 6.97 (d,1H,J=9 Hz), 7.53 (d,2H,J=9 Hz), 7.70 (m,3H), 8.27 (d,1H,J=9 Hz), and 8.31 (d,1H,J=9 Hz).

Example 2

Preparation of Compounds 7 and 8

Compounds 7 and 8 were prepared by the following reaction scheme:

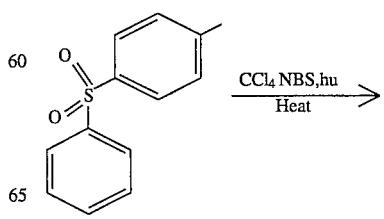

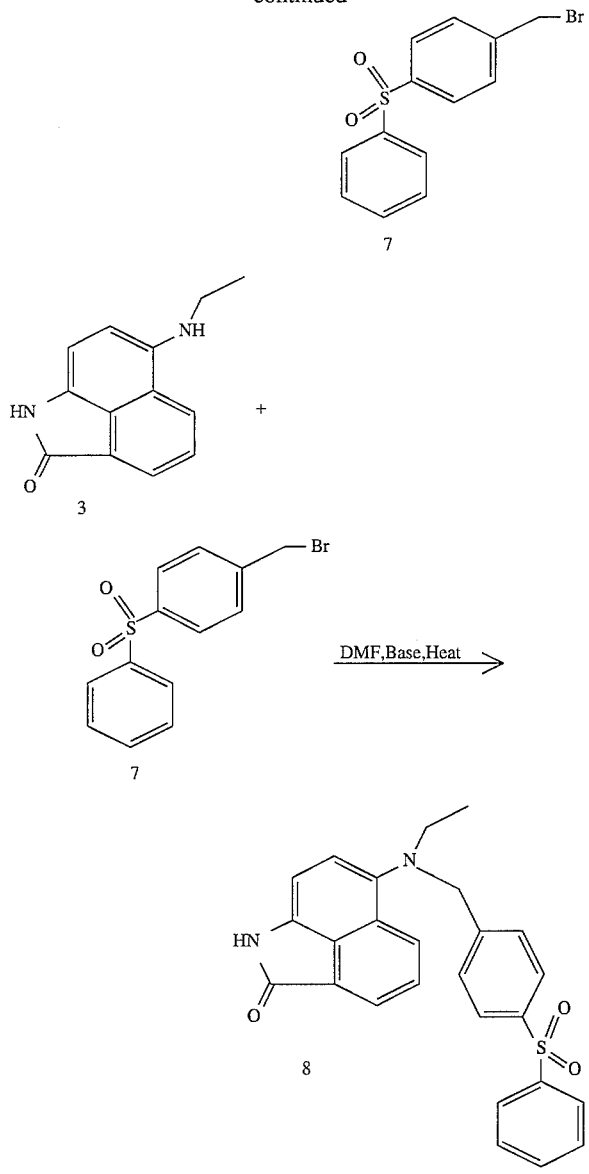

irradiated with a 200 W heat lamp for 30 minutes. After cooling, the mixture was filtered, and the solvent was removed under reduced pressure. The crude residue was chromatographed on flash silica gel (500 g) with ethyl acetate/petroleum ether (15:85). In this manner, there was obtained 17.4 g (86%) of the desired bromide as a white solid contaminated with about ten percent of the corresponding dibromide. Repeated chromatography and recrystallizations failed to remove the contaminate, and the material was used in the next step as such. IR (KBr) 1290, 1140, 1100, 720 cm$^{-1}$; $^1$H NMR (CDCl$_3$) δ 4.45 (s,2H,—CH$_2$Ar), 7.51–7.62 (m,5H), and 7.90–8.00 (m,4H). High Res. Mass Spec. Calcd. for C$_{13}$H$_{11}$O$_2$SBr: 309.9663. Found: 309.9648.

Preparation of Compound
8—N-[4-(phenylsulfonyl)benzyl]-N-ethyl-6-aminobenz[cd]indol-2(1H)-one To a rapidly stirred solution of 1.9 g (7.60 mmol) of N-ethyl-6-aminobenz[cd]indol-2(1H)-one hydrochloride (3) in 40 ml of DMF was added 3.2 ml (18.2 mmol) of diisopropylethylamine and 2.85 g (9.10 mmol) of 4-bromomethyldiphenylsulfone (7). The mixture was heated at 90° C. for 3 hours and then poured into water (500 ml). The aqueous layer was extracted with ethyl acetate (3×400 ml), and the combined organic layers were dried (anhydrous Na$_2$SO$_4$). After removal of the solvent under reduced pressure, the crude residue was chromatographed on flash silica gel (200 g) with a gradient of 0–20% ethyl acetate in CH$_2$Cl$_2$. In this manner, there was obtained 2.7 g (81%) of the desired product as an orange solid: m.p. 213°–216° C.; IR (KBr) 3140, 1300, 1140, 725 cm$^{-1}$, $^1$H, NMR (CDCl$_3$) δ 1.08 (t,3H,J=7 Hz,—CH$_3$), 3.20 (q,2H,J=7 Hz,—CH$_2$—), 4.38 (s,2H,—CH$_2$Ar), 6.81 (d,1H,J=7.5 Hz), 6.90 (d,1H,J=7.5 Hz), 7.45–7.60 (m,5H), 7.70 (t,1H,J=7 Hz), 7.81 (brs, 1H,N—H), 7.87 (d,2H,J=8.4 Hz), 7.93 (dd,2H,J=6.8,1.9 Hz), 8.07 (d,1H,J=7 Hz), and 8.26 (d,1H,J=8.07 Hz). Anal. Calcd. for C$_{26}$H$_{22}$N$_2$O$_3$S.0.5H$_2$O: C, 69.16; H, 5.13; N, 6.20; S, 7.10. Found: C, 68.88; H, 5.13; N, 5.96; S, 7.07. High Res. Mass Spec. Calcd. for C$_{26}$H$_{22}$N$_2$O$_3$S: 442.1351. Found: 442.1331.

Preparation of Compound
7—4-Bromomethyldiphenylsulfone

To a rapidly stirred solution of 15 g (64.6 mmol) of phenyl p-tolylsulfone in 300 ml of CCl$_4$ at 85° C. was added 11.5 g (64.6 mmol) of N-bromosuccinimide. The mixture was Example 3

Preparation of Compounds 9 through 16

Compounds 9 through 16 were prepared by the following reaction scheme:

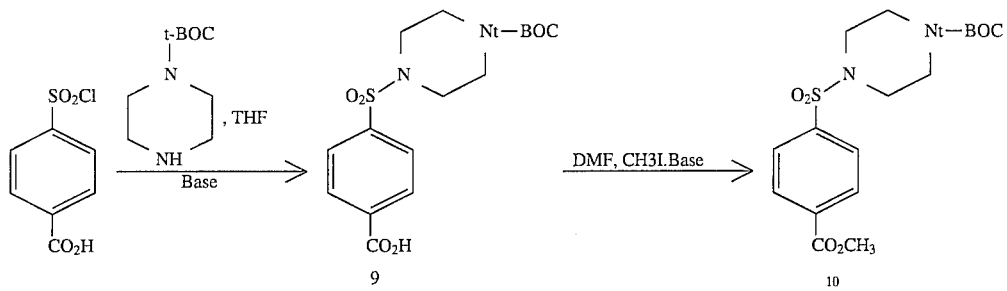

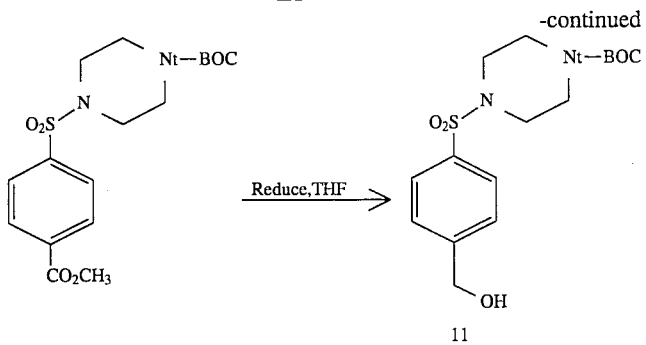
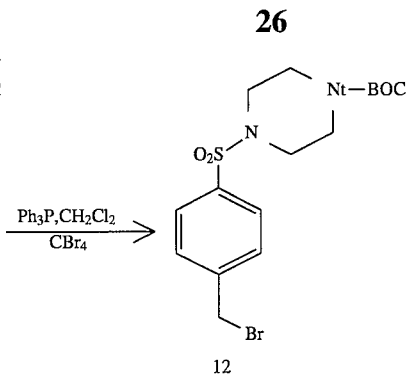
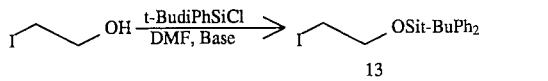
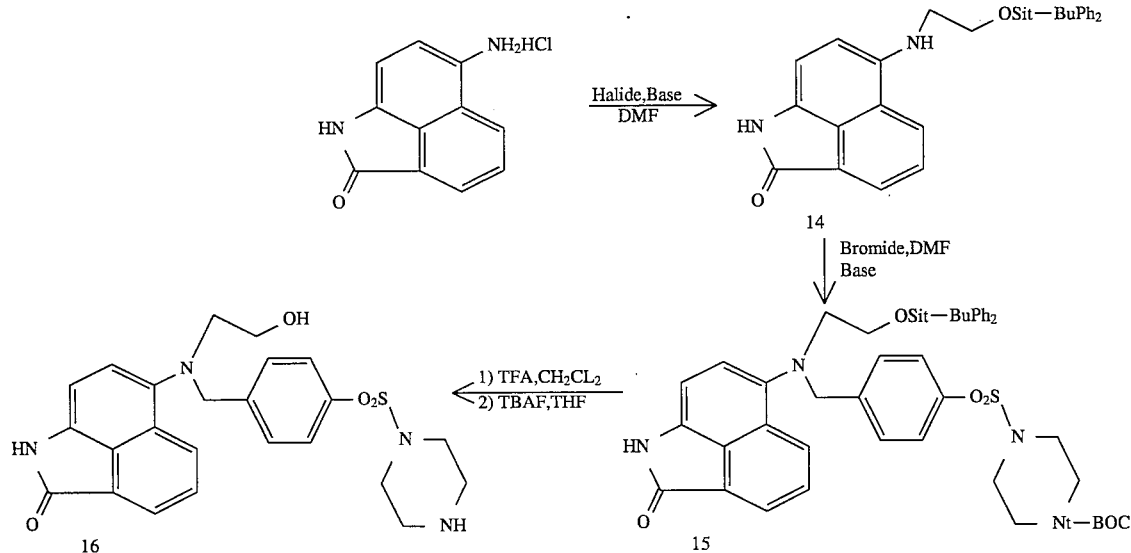

Preparation of Compound 9—N,N-(t-Butyl-1-piperazinecarboxylate)-4-carboxybenzenesulfonamide To a rapidly stirred solution of 40 g (215 mmol) of t-butyl-1-piperazinecarboxylate and 18.5 ml (128 mmol) of diisopropylethylamine in 300 ml of dry THF at 25° C. was added dropwise over a one hour period a solution of 23.7 g (107 mmol of 4-(chlorosulfonyl)benzoic acid in 200 ml of dry THF. The resulting mixture was stirred for an additional one hour and then poured into $H_2O$ (1000 ml). After extraction with ethyl acetate (300 ml which was discarded), the aqueous layer was acidified to pH 1 with concentrated HCl and then extracted with ethyl acetate (3×1000 ml). The combined organic layers were dried (anhydrous $Na_2SO_4$), and the solvent was removed under reduced pressure. In this manner, there was obtained 21 g (53%) of the desired acid as an off-white solid. $^1$H NMR ($D_6$DMSO) δ 1.33 (s,9H), 2.89 (brs,4H), 3.40 (brm,4H), 7.86 (d,2H,J=9 Hz), and 8.17 (d,2H,J=9 Hz). This material was fully characterized in the next step as the methyl ester.

Preparation of Compound 10—N,N-(t-Butyl-1-piperazinecarboxylate)-4-methoxycarbonylbenzenesulfonamide To a rapidly stirred solution of 21 g (56.7 mmol) of the acid (9) and 23.5 g (170 mmol) of $K_2CO_3$ in 300 ml of DMF at 25° C. was added 5.3 ml (85.1 mmol) of methyliodide. After 20 minutes, the mixture was poured into $H_2O$ (1000 ml), and the aqueous layer was extracted with ethyl acetate (3×1000 ml). The combined organic layers were dried (anhydrous $Na_2SO_4$), and the solvent was removed under reduced pressure. The crude residue was chromatographed on flash silica gel (600 g) with $EtOAc/CH_2Cl_2$ (5:95). In this manner, there was obtained 19.8 g (91%) of the desired ester as a white solid: m.p. 173.5°–174.5° C. ($EtOAc/CH_2Cl_2$ 3:1); IR (KBr) 2980, 2870, 1688, 1270, 1160, 1110, 940, 750 cm$^{-1}$; $^1$H NMR (CDCl$_3$) δ 1.40 (s,9H), 2.99 (brt,4H,J=5.3 Hz), 3.50 (brt,4H,J=5.3 Hz), 3.96 (s,3H), 7.82 (d,2H,J=7.4 Hz), and 8.20 (d,2H,J=7.4 Hz). Anal. Calcd. for $C_{17}H_{24}N_2O_6S$: C, 53.11; H, 6.29; N, 7.29; S, 8.34. Found: C, 53.21; H, 6.34; N, 7.14; S, 8.11.

Preparation of Compound 11—N,N-(t-Butyl-1-piperazinecarboxylate)-4-hydroxmethylbenzenesulfonamide To a rapidly stirred solution of 19.7 g (51.0 mmol) of the methyl ester (10) in 475 ml of THF at 0° C. under argon gas was added 116.7 ml (116.7 mmol) of a 1M solution of diisobutylaluminum hydride in hexane over a 5 minute period. After 30 minutes, 25 ml of a saturated aqueous solution of potassium, sodium tartrate was added, and the resulting mixture was stirred for 10 minutes. The mixture was then poured into 500 ml of 1:1 $H_2O$/saturated potassium, sodium tartrate, and the aqueous layer was extracted with CH$_2$Cl$_2$ (4×400 ml). The combined organic layers were dried (anhydrous Na$_2$SO$_4$), and the solvent was removed under reduced pressure. The crude residue was chromatographed on flash silica gel (500 g) with EtOAc/CH$_2$Cl$_4$ (1:4). In this manner, there was obtained 17.0 g (93%) of the desired alcohol as a white solid: m.p. 170°–171.5° C. (EtOAc/CH$_2$Cl$_2$,1:1); IR (KBr) 3450, 2980, 1660, 1430, 1345, 1270, 1160, 930, 720 cm$^{-1}$; $^1$H NMR (CDCl$_3$) δ 1.39 (s,9H), 2.10 (t,1H, J=5.1 Hz,—OH), 2.95 (t,4H,J=4.94 Hz), 3.49 (t,4H,J=4.94 Hz), 4.80 (d,2H,J=5.1 Hz), 7.53 (d,2H,J=8.2 Hz), 7.72 (d,2H,J=8.2 Hz). Anal. Calcd. for C$_{16}$H$_{24}$N$_2$O$_5$S: C, 53.91; H, 6.79; N, 7.86; S, 9.00. Found: C, 54.10; H, 6.70; N, 7.63; S, 8.72.

Preparation of Compound
12—N-N-(t-Butyl-1-piperazinecarboxylate)-4-bromomethylbenzenesulfonamide To a rapidly stirred solution of 4.4 g (16.8 mmol) of triphenylphosphine and 5.6 g (16.8 mmol) of CBr$_4$ in 80 ml of CH$_2$Cl$_2$ at 25° C. was added as a solid 4.0 g (11.2 mmol) of the alcohol (11). After 20 minutes, the mixture was poured into water (400 ml), and the aqueous layer was extracted with CH$_2$Cl$_2$ (2×400 ml). The combined organic layers were dried (anhydrous Na$_2$SO$_4$), and the solvent was removed under reduced pressure. The crude residue was chromatographed on flash silica (200 g) with Et$_2$O/CH$_2$Cl$_2$ (1.5:98.5). In this manner, there was obtained 4.53 g (96%) of the desired bromide as a white solid: m.p. 155°–156° C. (decomp.); IR (KBr) 2980, 2860, 1680, 1410, 1350, 1240, 1160, 930, 845, 740, 730 cm$^{-1}$; $^1$H NMR (CDCl$_3$) δ 1.40 (s,9H), 2.98 (t,4H,J=4.9 Hz), 3.50 (t,4H,J=4.9 Hz), 4.49 (s,2H,—CH$_2$Br), 7.56 (d,2H,J=8.3 Hz) and 7.72 (d,2H,J=8.3 Hz). Anal. Calcd. for C$_{16}$H$_{23}$N$_2$O$_4$SBr: C, 45.83; H, 5.53; N, 6.68; Br, 19.06. Found: C, 45.66; H, 5.59; N, 6.44; Br, 19.04.

Preparation of Compound
13—2-tert-Butyldiphenylsilylether-1-iodoethane 2-hydroxy-1-iodoethane (2.26 ml, 29.1 mmol) was added to a 100 ml round bottom flask containing tert-butylchlorodiphenylsilane (8.79 g, 32.0 mmol), triethylamine (5.26 ml, 37.8 mmol), and a catalytic amount of 4-dimethylaminopyridine (0.183 g, 1.5 mmol) in methylene chloride at 0° C. A precipitate was formed after the addition of 2-hydroxy-1-iodoethane. The solution was stirred at 0° C. for 1.5 hour. The reaction was then stopped, and the solid was filtered. Distilled water (30 ml) was added to the flask containing the filtrate, and the organic layer was separated. The aqueous layer was then extracted with methylene chloride (20 ml×3). The organic portions were combined and dried with anhydrous Na$_2$SO$_4$. Removing of the solvent via rotor-evaporation gave 11.9 g of an oil. $^1$H NMR:d 1.07 (9H,s), 3.19–3.24 (2H,t,J=6.7 Hz), 3.84–3.88 (2H,t,J=6.7 Hz), 7.36–7.44 (6H, m), and 7.65–7.69 (4H,m). IR (cm$^{-1}$), 3500 (w), 3060–3080 (w), 2960 (m), 2940 (m), 2888 (m), 2860 (m), 1700–1950 (w), 1460–1470 (m), 1270 (m), 1190 (m), 1170 (m), 1080–1100 (s), 700 (s), 500 (s).

Preparation of Compound
14—N-(2-tert-Butyldiphenylsiloxyethyl)-6-aminobenz[cd]indol-2(1H)-one To a rapidly stirred solution of 700 mg (3.17 mmol) of 6-aminobenz[cd]indol-2(1H)-one hydrochloride (2) and 1.4 ml (9.90 mmol) of diisopropylethylamine in 10 ml of DMF at 120° C. was added 1.86 g (4.5 mmol) of 2-tert-butyldiphenylsiloxy-1-iodothane (13). After 3 hours, the reaction was poured into H$_2$O (150 ml), and the aqueous layer was extracted with ethyl acetate (3×90 ml). The combined organic layers were dried (anhydrous Na$_2$SO$_4$), and the solvent was removed under reduced pressure. The crude residue was chromatographed on flash silica gel (150 g) with EtOAc/CH$_2$Cl$_2$ (15:85). In this manner, there was obtained 581 mg (38%) of the desired product as a red/orange foam: IR (KBr) 3200, 2930, 2860, 1630, 1450, 1260, 1080, 700 cm$^{-1}$; $^1$H NMR (CDCl$_3$) δ 1.58 (s,9H), 3.38 (m,2H,—NCH$_2$—), 4.02 (t,2H,J=5 Hz,—OCH$_2$—), 4.85 (brs,1H,—NH—), 6.31 (d,1H,J=7.7 Hz), 6.78 (d,1H,J=7.7 Hz), 7.30–7.48 (m,6H), 7.63–7.71 (m,5H), 7.91 (d,1H,J=8.2 Hz), 8.10 (d,1H,J=7.0 Hz). High Res. Mass Spec. Calcd. for C$_{29}$H$_{30}$N$_2$O$_2$Si: 466.2077. Found: 466.2076.

Preparation of Compound 15—N-[4-(N,N-t-Butoxycarbonylpiperazinylsulfamoyl)benzyl]-N-(2-t-butyldiphenylsiloxyethyl)-6-aminobenz[cd]indol-2(1H)-one To a rapidly stirred solution of 575 mg (1.2 mmol) of the amine (14) and 0.27 ml (1.56 mmol) of diisopropylethylamine in 5 ml of DMF at 90° C. was added 557 mg (1.33 mmol) of N,N-(t-butyl-1-piperazinecarboxylate)-4-bromomethyl benzenesulfonamide (12). After 3 hours, an additional 55 mg (0.13 mmol) of the bromide was added. After two additional hours, the mixture was poured into water (120 ml), and the aqueous layer was extracted with ethyl acetate (3×100 ml). The combined organic layers were dried (anhydrous Na$_2$SO$_4$), and the solvent was removed under reduced pressure. The crude residue was chromatographed on flash silica gel (50 g) with Et$_2$O/CH$_2$Cl$_2$ (1:4). In this manner, there was obtained 878 mg (90%) of the desired product as an orange foam: IR (KBr) 2930, 2860 1680, 1640, 1240, 920, 700 cm$^{-1}$; $^1$H NMR (CDCl$_3$) δ 1.02 (s,9H), 140 (s,9H), 2.93 (t,4H,J=5.0 Hz), 3.41 (t,2H,J=5.4 Hz), 3.49 (t,4H,J=4.8 Hz), 3.81 (t,2H,J=5.6 Hz), 4.51 (s,2H), 6.70 (d,1H,J=7.5 Hz), 6.81 (d,1H,J=7.5 Hz), 7.20–7.30 (m,4H), 7.34–8.02 (m,2H), 7.55 (d,4H,J=6.6 Hz), 7.60–7.73 (m,3H), 7.80 (brs,1H,—NH—), 8.08 (d,1HJ=6.9 Hz), 8.38 (d,1H,J=8.1 Hz). High Res. Mass Spec. Calcd. for C$_{45}$H$_{52}$N$_4$O$_6$SSi: 804.3377. Found: 804.3375.

Preparation of Compound
16—N-[4-(N,N-Piperazinylsulfamoyl)benzyl]-N-hydroxyethyl-6-aminobenz[cd]indol-2(1H)-one To a rapidly stirred solution of 870 mg (1.08 mmol) of the lactam (15) in 15 ml of CH$_2$Cl$_2$ at 25° C. was added 1.5 ml of trifluoroacetic acid. After 6 hours, the solvent was removed under reduced pressure. The crude residue was dissolved in 15 ml of THF and to this mixture was added 6.6 ml (6.48 mmol) of a 1M solution of tetrabutylammonium fluoride in THF. The mixture was then heated to reflux. After 24 hours, the mixture was poured into H$_2$O (200 ml), and NaCl was added to the saturation point. To the aqueous layer was added saturated NaHCO$_3$ (30 ml), and the mixture was extracted with ethyl acetate (6×200 ml). The combined organic layers were dried (anhydrous Na$_2$SO$_4$) and the solvent was removed under reduced pressure. The crude residue was chromatographed on flash silica gel (50 g) using a gradient of 0–12% MeOH in CH$_2$Cl$_2$. In this manner, there was obtained 425 mg (84%) of the desired material as a bright orange solid: m.p. 98° C. (decomp.); IR (KBr) 3190, 2940, 2840, 1670, 1320, 1240, 1160, 730 cm$^{-1}$; $^1$H NMR (D$_6$DMSO) δ 2.68 (m,8H), 3.26 (m,2H), 3.58 (m,2H), 4.53 (S,2H,—NCH$_2$Ar), 4.66 (t,1H,J=5 Hz,—OH), 6.80 (d,1H, J=7.5 Hz), 7.05 (d,1H, J=7.5 Hz), 7.61 (m,4H), 7.77 (t,1H, J=7.1 Hz), 7.97 (d,1H,J=6.9 Hz), 8.42 (d,1H,J=8.2 Hz), and 10.59 (s,1H,—NH). High Res. Mass Spec. Calcd. for $C_{24}H_{26}N_4O_4S$: 466.1675. Found: 466.1700.

Example 4

Preparation of Compounds 17 through 19

Compounds 17 through 19 were prepared by the following reaction scheme:

was extracted with ethyl acetate (2×80 ml). The combined organic layers were dried (anhydrous $Na_2SO_4$), and the solvent was removed under reduced pressure. The crude residue was chromatographed on flash silica gel (30 g) with $EtOAc/CH_2Cl_2$ (1:9). In this manner, there was obtained 610 mg (81%) of the desired material as orange needles: m.p. 115° C. (decomp.) (EtOAc/petroleum ether 3:1); IR (KBr) 2970, 2930, 2870, 1680, 1410, 1345, 1250, 1160, 930, 730 $cm^{-1}$; $^1H$ NMR ($CDCl_3$) δ 0.86 (t,3H,J=7.3 Hz), 1.40 (s,9H), 1.59 (m,2H), 2.94 (t,4H,J=5.1 Hz), 3.12 (t,2H,J=5.9 Hz),

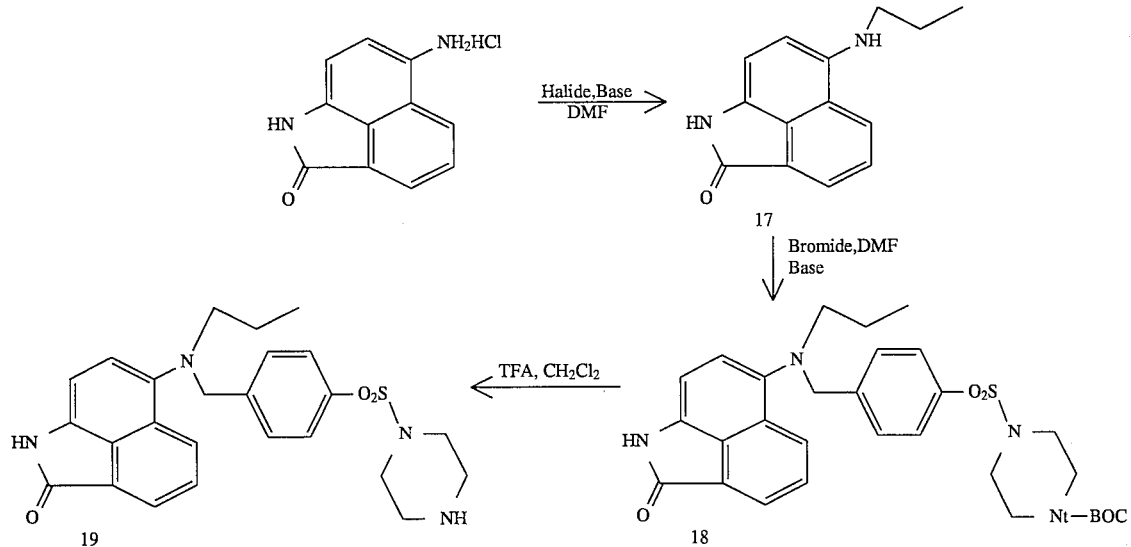

Preparation of Compound 17—N-Propyl-6-aminobenz[cd]indol-2(1H)-one

To a rapidly stirred solution of 500 mg (2.27 mmol) of 6-aminobenz[cd]indol-2-(1H)-one hydrochloride (2) and 1.0 ml (7.04 mmol) of diisopropylethylamine in 8 ml of DMF at 120° C. was added 0.26 ml (2.72 mmol) of propyliodide. After 2 hours, the mixture was poured into $H_2O$ (120 ml) and the aqueous layer was extracted with ethyl acetate (3×100 ml). The combined organic layers were dried (anhydrous $Na_2SO_4$), and the solvent was removed under reduced pressure. The crude residue was chromatographed on flash silica gel (50 g) with $EtOAc/CH_2Cl_2$ (15:85). In this manner, there was obtained 320 mg (62%) of the desired material as a red solid: m.p. 166°–167° C. (EtOAc); IR (KBr) 3140, 1660, 1630, 1450, 1260, 760 $cm^{-1}$; $^1H$ NMR ($CDCl_3$) δ 1.08 (t,3H,J=7.4 Hz), 1.79 (tq,2H,J=7.4,7.0 Hz), 3.22 (t,2H,J=7.70 Hz), 4.31 (brs,1H,HNAr), 6.38(d,1H,J=7.7 Hz), 6.84 (d,1H, J=7.7 Hz), 7.68 (dd,1H,J=7.1,7.1 Hz), 8.03 (d,1H,J=7.1 Hz), 8.05 (brs,1H,NH), and 8.10(d,1H,J=7.03). Anal. Calcd. for $C_{14}H_{14}N_2O$: C, 74.31; H, 6.24; N, 12.38. Found: C, 74.14; H, 6.40; N, 12.19.

Preparation of Compound 18—N-[4-(N,N-t-Butoxycarbonylpiperazinylsulfamoyl)benzyl]-N-propyl-6-aminobenz[cd]indol-2(1H)-one To a rapidly stirred solution of 300 mg (1.33 mmol) of the amine (17) and 0.35 ml (2.0 mmol) of diisopropylethylamine in 4 ml of DMF at 105° C. was added 667 mg (1.60 mmol) of N,N-(t-butyl-1-piperazinecarboxylate)-4-bromomethyl benzenesulfonamide (12). After 14 hours, the mixture was poured into $H_2O$ (40 ml), and the aqueous layer 3.49 (t,4H,J=5.1 Hz), 4.42 (s,2H,—$NCH_2$—), 6.81 (d,1H, J=7.6 Hz), 6.91 (d,1H,J=7.6 Hz), 7.51 (d,2H,J=8.3 Hz), 7.66 (d,2H,J=8.3 Hz), 7.73 (t,1H,J=7.1 Hz), 8.07 (brs,1H,—NH), 8.09 (d,1H,J=7.1 Hz), and 8.31 (d,1H,J=7.1 Hz). Anal. Calcd. for $C_{30}H_{36}N_4O_5S$: C, 63.81; H, 6.43; N, 9.92; S, 5.68. Found: C, 63.72; H, 6.50; N, 9.73; S, 5.52.

Preparation of Compound 19—N-[4-(N,N-Piperazinylsulfamoyl)benzyl]-N-propyl-6-aminobenz[cd]indol-2(1H)-one To a rapidly stirred solution of 545 mg (0.96 mmol) of the amine (18) in 15 ml of $CH_2Cl_2$ at 25° C. was added 1.5 ml of trifluoroacetic acid. After 2 hours, the mixture was poured into saturated $NaHCO_3$ (100 ml), and the aqueous layer was extracted with ethyl acetate (3×140 ml). The combined organic layers were dried (anhydrous $Na_2SO_4$), and the solvent was removed under reduced pressure. The crude residue was recrystallized from ethyl acetate/petroleum ether (3:1). In this manner, there was obtained 375 mg (84%) of the desired material as an orange solid: m.p. 187°–189° C.; IR (KBr) 3180, 2940, 2835, 1640, 1445, 1410, 1315, 1160, 1090, 935, 730 $cm^{-1}$; $^1H$ NMR ($CDCl_3$) δ 0.87 (t,3H,J=7.3 Hz), 1.60 (m,2H), 2.88–3.02 (M,8H), 3.11 (t,2H, J=5.8 Hz), 4.42 (s,2H), 6.83 (d,1H,J=7.5 Hz), 6.93 (D,1H, J=7.5 Hz), 7.52 (d,2H,J=8.3 Hz), 7.67 (d,2H,J=8.3 Hz), 7.73 (t,1H,J=7 1 Hz), 7 80 (brs,1H), 8.09 (d, 1H J=70 Hz ), and 8.31 (d, 1H, J=7.8 Hz). Anal Calcd for $C_{25}H_{28}N_4O_3S$: C, 64.63; H, 6.07; N, 12.06; S, 6.90. Found: C, 64.44; H, 6.27; N, 11.82; S, 6.71.

Example 5

Preparation of Compounds 20 through 22

Compounds 20 through 22 were prepared in accordance with the following reaction scheme:

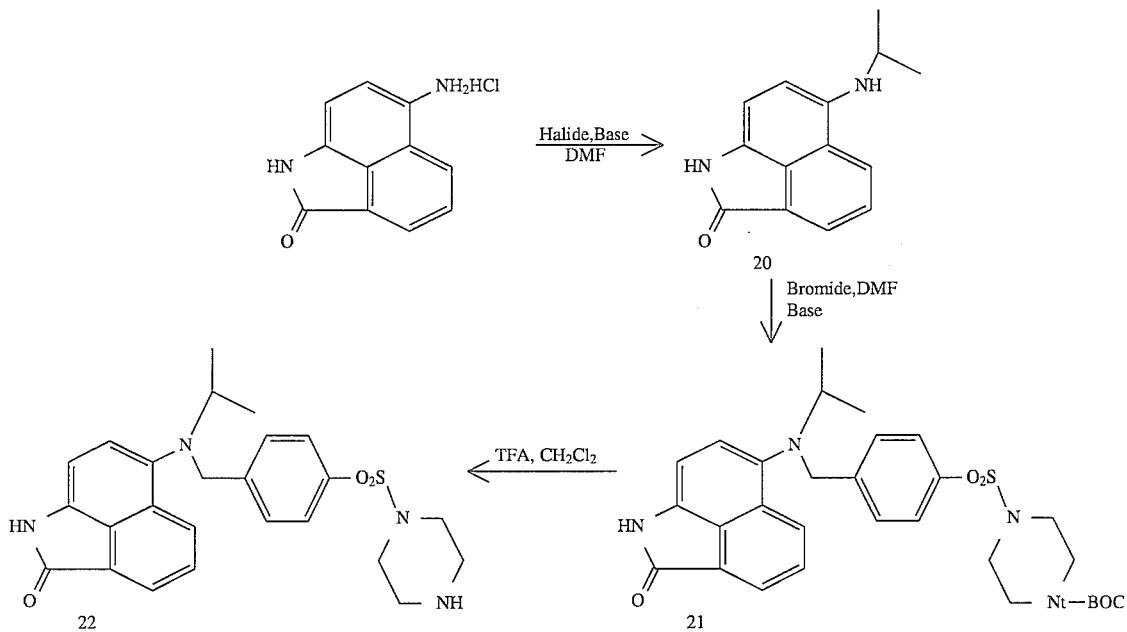

Preparation of Compound 20—N-Isopropy-6-Aminobenz[cd]indol-2(1H)-one

The amine (20) was prepared in similar fashion to Compound 38 below using 2-iodopropane. After workup, the crude residue was flash chromatographed on silica, eluting with hexane:ethyl acetate (1:1). In this manner, there was obtained (20) in 38% yield as a red solid. $^1$H NMR (CDCl$_3$) δ 1.32 (s,3H), 1.34 (s,3H), 3.77 (m,1H), 4.14 (bs,1H), 6.40 (d,1H,J=7.8 Hz), 6.86 (d,1H,J=7.7 Hz), 7.67 (t,1H,J=7.1 Hz), 8.01 (d,1H,J=8.3 Hz), 8.10 (d,1H,J=7.0 Hz), 8.38 (bs,1H). Anal. Calcd for $C_{14}H_{14}N_2O$ (exact mass): 226.1106. Found: 226.1105.

Preparation of Compound 21—N-Isopropylamino-4-methylphenylsulfonyl-t-butyl-1-piperazine carboxylate-6-aminobenz[cd]indol-2(1H)-one The amine was (21) was prepared in similar fashion to the preparation of (38) below. The crude residue was flash chromatographed on silica eluting methylene chloride:ethyl acetate (9:1). In this manner, there was obtained in 62% yield an orange brittle foam. IR (KBr) 3200, 2930, 1650, 1250 cm$^{-1}$. $^1$H NMR (CDCl$_3$) δ 1.27 (s,3H), 1.30 (s,3H), 1.38 (s,9H), 2.85 (m,4H), 3.44 (m,4H), 3.82 (m, 1H), 4.43 (s,2H), 6.72 (d,1H,J=7.6 Hz), 6.89 (d,1H,J=7.6 Hz), 7.50 (m,4H), 7.75 (t,1H,J=7.1 Hz), 8.02 (bs,1H), 8.07 (d,2H,J=7.0 Hz), and 8.30 (d,1H,J=8.2 Hz). Anal. Calcd for $C_{30}H_{36}N_4O_5S$ (exact mass): 564.2406 Found: 564.2446.

Preparation of Compound 22—N-[4-(N,N-piperazinylsulfamoyl)benzyl]-N-isopropyl-6-aminobenz[cd]indol-2(1H)-one To a rapidly stirred solution of 295 mg (0.52 mmol) of the amine (21) in 8 ml of CH$_2$Cl$_2$ at 25° C. was added 1 ml of trifluoracetic acid. After 3 hours, the mixture was poured into saturated NaHCO$_3$ (60 ml), and the aqueous layer was extracted with ethyl acetate (3×100 ml). The combined organic layers were dried (anhydrous Na$_2$SO$_4$), and the solvent was removed under reduced pressure. The crude residue was chromatographed on flash silica gel (30 g) with MeOH/CH$_2$Cl$_2$ (5:95). In this manner, there was obtained 177 mg (73%) of the desired material as an orange foam: IR (KBr) 2960, 1665, 1640, 1440, 1340, 1320, 1250, 1155, 1090, 940, 730 cm$^{-1}$; $^1$H NMR (CDCl$_3$) δ 1.28 (d,6H,J=6.5 Hz), 2.85 (brs,8H,—NCH$_2$CH$_2$N—), 3.80 (sep,1H,J=6.5 Hz), 4.41 (s,2H,—NCH$_2$Ar), 6.75 (d,1H,J=7.6 Hz), 6.93 (d,1H,J=7.6 Hz), 7.48–7.56 (m,4H), 7.75 (t,1H, J=7.1 HZ, 7.91 (brs, 1H ), 8.06 (d,1H,J=7.1 Hz) , and 8.31 (d,1H,J=7.1 Hz). High Res. Mass Spec. Calcd. for $C_{25}H_{28}N_4O_3S$: 464.1882. Found: 464.1860.

Example 6

Preparation of Compounds 23 and 24

Compounds 23 and 24 are prepared according to the following reaction scheme:

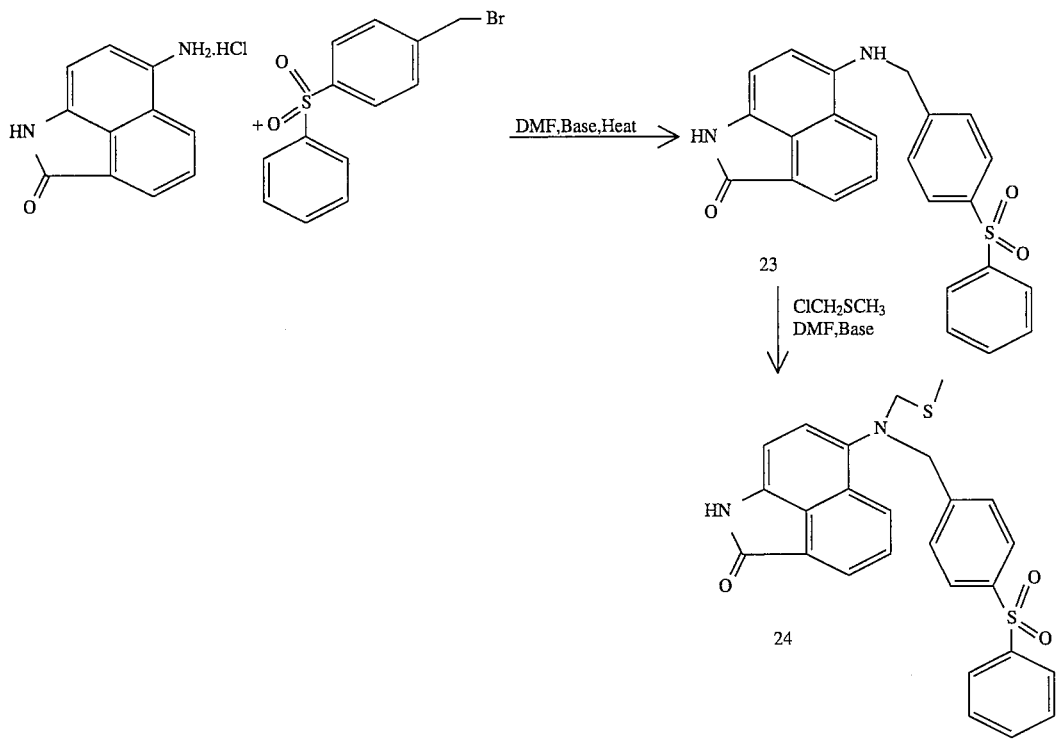

Preparation of Compound 23—N-[4-(Phenylsulfonyl)benzyl]-6-aminobenz[cd]indol-2(1H)-one To a rapidly stirred solution of 300 mg (1.36 mmol) of mmol) of diisopropylethylamine in 5 ml of DMF at 75° C. was added 507 mg (1.6 mmol) of 4-bromomethyldiphensylsulfone (7). After 3 hours, the mixture was poured into H$_2$O, and the aqueous layer was extracted with ethyl acetate (3×100 ml). The combined organic layers were dried (anhydrous Na$_2$SO$_4$), and the solvent was removed under reduced pressure. The crude residue was crystallized from EtOH to give 403 mg (71%) of the desired product as an orange solid: m.p. 196°–212° C. (decomp.); IR (KBr) 1630, 1450 1265, 1150, 1100, 725 cm$^{-1}$; $^1$H NMR (D$_6$DMSO) δ 4.51 (brs, 2H,—NCH$_2$Ar), 6.05 (d,1H,J=7.7 Hz), 6.63 (d,1H,J=7.7 Hz), 7.15 (brs,1H,—NH—R), 7.55–7.75 (m,6H), 7.88–7.98 (m,5H), 8.47 (d,1H,J=8.1 Hz), and 10.35 (s,1H,—NH—C=O). High Res. Mass Spec. Calcd. for C$_{24}$H$_{18}$N$_2$O$_2$S: 414.1038. Found: 414.1032.

Preparation of Compound 24—N-[4-(Phenylsulfonyl)benzyl]-N-methylthiomethyl-6-aminobenz[cd]indol-2(1H)-one To a rapidly stirred solution of 260 mg (0.62 mmol) of the amine (23) and 0.26 ml (1.49 mmol) of diisopropylethylamine in 6 ml of DMF at 120° C. was added dropwise 0.10 ml (1.25 mmol) of chloromethylmethyl sulfide. After 1.5 hours, the mixture was poured into 1:1 saturated NaHCO$_3$/H$_2$O (100 ml), and the aqueous layer was extracted with ethyl acetate (3×100 ml). Each ethyl acetate layer was back washed with H$_2$O (2×50 ml). The combined organic layers were dried (anhydrous Na$_2$SO$_4$), and the solvent was removed under reduced pressure. The crude residue was chromatographed on flash silica gel (30 g) with a gradient of 0–10% EtOAc/CH$_2$Cl$_2$. In this manner, there was obtained 59 mg (20%) of chromatographed on flash silica gel (30 g) with a gradient of 0–10% EtOAc/CH$_2$Cl$_2$. In this manner, there was obtained 59 mg (20%) of the desired product as an orange solid: m.p. 170°–180° C. (decomp.) (EtOAc/CH$_2$Cl$_2$ 3:1); IR (KBr) 3190, 1630–1690, 1445, 1300, 1145, 1100, 725 cm$^{-1}$; $^1$H NMR (CDCl$_3$) δ 1.78 (s,3H,—SCH$_3$), 4.48 (s,2H), 4.57 (s,2H), 6.83 (d,1H,J=7.5 Hz), 7.08 (d,1H,J=7.5 Hz), 7.48–7.60 (m,5H), 7.71 (brs, 1H,—NH—C=O), 7.76 (t,1H,J=7.2 Hz), 7.88 (d,2H,J=8.3 Hz), 7.93 (d,2H,J=8.1 Hz), 8.09 (d,1H,J=7.0 Hz), and 8.26 (d,1H,J=8.3 Hz). High Res. Mass Spec. Calcd. for C$_{26}$H$_{22}$N$_2$O$_3$S$_2$: 474.1072. Found: 474.1071.

Example 7

Preparation of Compounds 25 through 27

Compounds 25 through 27 were prepared according to the following reaction scheme:

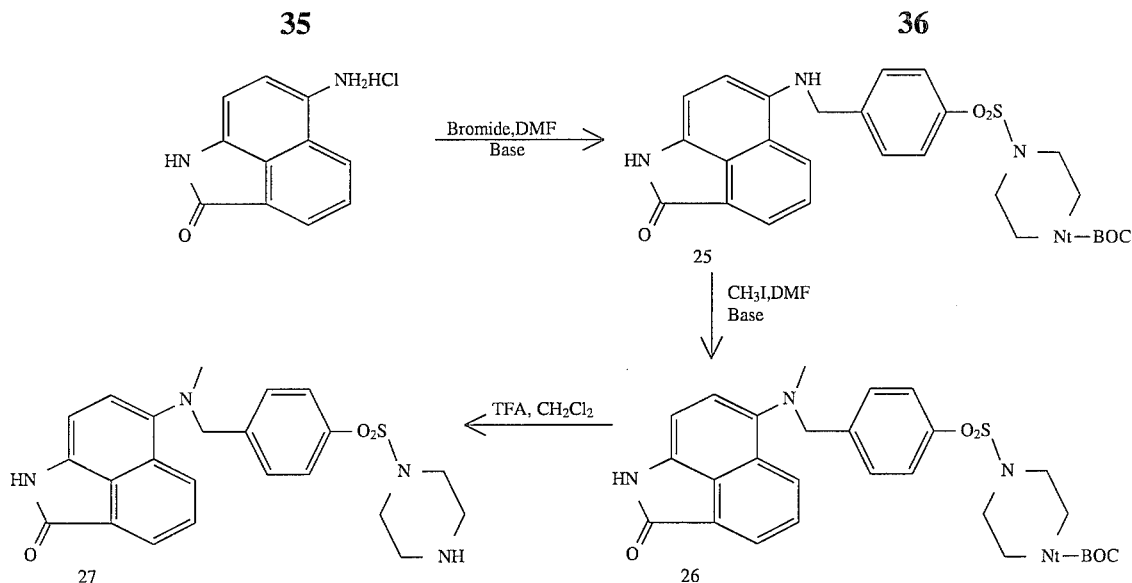

Preparation of Compound 25—N-[4-(N,N-t-Butoxycarbonylpiperazinylsulfamoyl)benzyl-6-aminobenz[cd]indol-2(1H)-one To a rapidly stirred solution of 500 mg (2.26 mmol) of 6-aminobenz[cd]indol-1(1H)-one hydrochloride (2) and 0.9 ml (5.20 mmol) of diisopropylethylamine in 6 ml of DMF at 75° C. was added 1.04 g (2.49 mmol) of N,N-(t-butyl-1-piperazinecarboxylate)-4-bromomethylbenzenesulfonamide (12). After 3 hours, the mixture was poured into H$_2$O (150 ml), and the aqueous layer was extracted with ethyl acetate (3×90 ml). The combined organic layers were dried (anhydrous Na$_2$SO$_4$), and the solvent was removed under reduced pressure. The crude residue was chromatographed on flash silica gel (50 g with EtOAc/CH$_2$Cl$_2$ (3:7)). In this manner, there was obtained 513 mg (43%) of the desired material as an orange solid: m.p. 174°–180° C. (decomp.) (EtOAc/CH$_2$Cl$_2$ 2:1); IR (KBr) 2980, 1650, 1400, 1325, 1250, 1160, 925, 730 cm$^{-1}$; $^1$H NMR (D$_6$DMSO) δ 1.31 (s,9H), 2.80 (m,4H), 3.36 (m,4H), 4.56 (d,2H,J=5.8 Hz,—NCH$_2$Ar), 6.10 (d,1H,J=7.7 Hz), 6.65 (d,1H,J=7.7 Hz), 7.15 (brs,1H, —NH—), 7.65–7.80 (m,5H), 7.96 (d,1H,J=7.04 Hz), 8.49 (d,1H,J=8.2 Hz), and 10.37 (s,1H,—NHC═O). Anal. Calcd. for C$_{27}$H$_{30}$N$_4$O$_5$S: C, 61.05; H, 5.79; N, 10.72; S, 6.14. Found: C, 62.02; H, 5.80; N, 10.64; S, 5.95.

Preparation of Compound 26—N-[4-(N,N-t-Butoxycarbonylpiperazinylsulfamoyl)benzyl-N-methyl-6-aminobenz[cd]indol-2(1H)-one To a rapidly stirred solution of 150 mg (0.29 mmol) of the amine (25) and 65 µl (0.37 mmol) of diisopropylethylamine in 2 ml of DMF at 90° C. was added 20 µl (0.32 mmol) of methyl iodide. After 2 hours, an additional 20 µl (0.32 mmol) of methyl iodide was added. The mixture was stirred for 2 hours more, and another 20 µl (0.32 mmol) of methyl iodide was then added. After an additional two hours, the mixture was poured into H$_2$O/saturated aqueous NaHCO$_3$ 1:1 (50 ml), and the aqueous layer was extracted with ethyl acetate (3×60 ml). Each organic layer was washed with H$_2$O (2×50 ml). The combined organic layers were then dried (anhydrous Na$_2$SO$_4$), and the solvent was removed under reduced pressure. The crude residue was chromatographed on flash silica gel (20 g) with EtOAc/CH$_2$Cl$_2$ (1:4). In this manner, there was obtained 80 mg (52%) of the desired product as an orange form: IR (KBr) 2980, 2860, 1670, 1400, 1350 1250, 1160, 930, 730 cm$^{-1}$; $^1$H NMR (CDCl$_3$ δ 1.40 (s,9H), 2182 (s,3H,—NCH$_3$), 2.99 (brt,4H,J=5.0 Hz), 3.51 (brt,4H,J=5.1 Hz), 4.41 (s,2H,—NCH$_2$Ar), 6.89 (s,2H), 7.61 (d,2H,J=8.3 Hz), 7.66–7.75 (m,3H), 8.09 (d,1H,J=7.0 Hz), 8.23 (d,1H,J=8.2 Hz), and 9.06 (s,1H,—NCH═O). High Res. Mass Spec. Calcd. for C$_{28}$H$_{32}$N$_4$O$_5$S: 536.2093. Found: 536.2084.

Preparation of Compound 27—N-[4-(N,N-Piperazinylsulfamoyl)benzyl]-N-methyl-6-aminobenz[cd]indol-2(1H)-one To a rapidly stirred solution of 75 mg (0.14 mmol) of the amine (26) in 2 ml of CH$_2$Cl$_2$ was added 0.2 ml of trifluoroacetic acid at 25° C. After 3 hours, the mixture was poured into saturated NaHCO$_3$ (50 ml), and the aqueous layer was extracted with ethyl acetate (4×60 ml). The combined organic layer was dried (anhydrous Na$_2$SO$_4$), and the solvent was removed under reduced pressure. The crude residue was chromatographed on flash silica gel (20 g) with MeOH/CH$_2$Cl$_2$ (5:95). In this manner, there was obtained 48 mg (79%) of the desired material as an orange solid: m.p. 176°–178° C.; IR (KBr) 3280, 1680, 1340, 1260, 1160, 900, 720 cm$^{-1}$; $^1$H NMR (D$_6$DMSO) δ 2.68 (m,4H), 276 (m,7H), 4.42 (s,2H,—NCH$_2$Ar), 6.84 (d,1H,J=7.3 Hz), 6.96 (d,1H, J=7.3 Hz), 7.65–7.72 (m,4H), 7.78 (y,1H,J=7.7 Hz), 7.99 (d,1H,J=7.3 Hz), 8.25 (d,1H,J=8.2 Hz), and 10.63 (s,1H,—NHC═O). High Res. Mass Spec. Calcd. for C$_{23}$H$_{24}$N$_4$O$_3$S: 436.1569. Found: 436.1557.

Example 8

Preparation of Compounds 28 and 29

Compounds 28 and 29 were prepared according to the following reaction scheme:

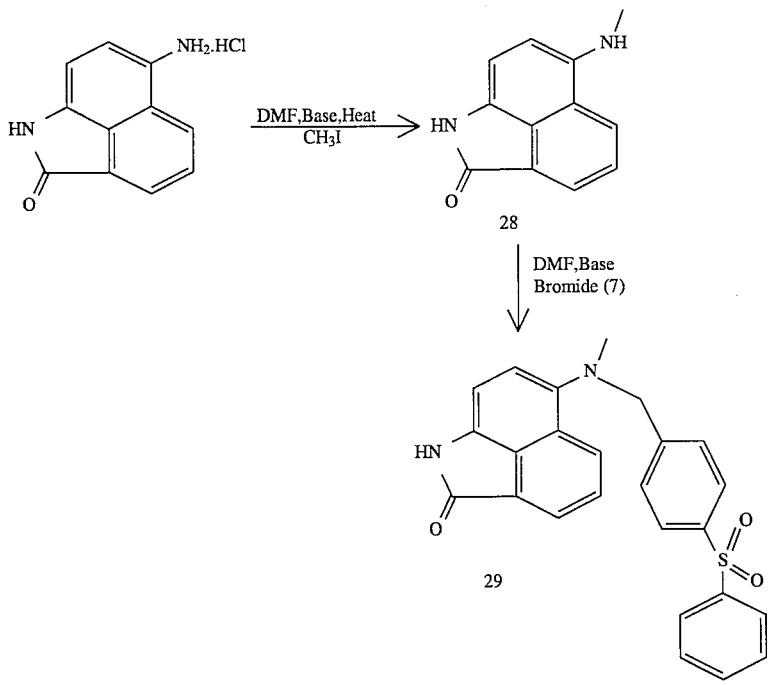

Preparation of Compound 28—N-Methyl-6-aminobenz[cd]indol-2(1H)-one

To a rapidly stirred solution of 690 mg (3.13 mmol) of 6-aminobenz[cd]indol-2(1H)-one hydrochloride (2) and 1.25 ml (7.20 mmol) of diisopropylethylamine in 5 ml of DMF at 70° C. was added 0.2 ml (3.44 mmol) of methyliodide. After 2 hours, the mixture was poured into $H_2O$/saturated $NaHCO_3$ (1:1), and the aqueous layer was extracted with ethyl acetate (3×100 ml). The combined organic layers were dried (anhydrous $Na_2SO_4$), and the solvent was removed under reduced pressure. The crude residue was chromatographed on flash silica gel (50 g) with MeOH/$CH_2Cl_2$ (2.98). In this manner, there was obtained 232 mg (37%) of the desired material as a red solid: m.p. 237°–240° C. (EtOAc/MeOH 2:1); IR (KBr) 3180, 1610, 1520, 1450, 1380, 1270, 770, 745 $cm^{-1}$; $^1H$ NMR ($D_6$DMSO) δ 2.81 (brs,3H), 6.19 (d,1H,J=7.7 Hz), 6.44 (m, 1H,—NH—), 6.78 (d,1H,J=7.7 Hz), 7.67 (t,1H,J=7.2 Hz), 7.93 (d,1H,J=7.0 Hz), 8.35 (d,1H,J=8.2 Hz), and 10.38 (s,1H,—NHC=O). Anal. Calcd. for $C_{12}H_{10}N_2O$: C, 72.71; H, 5.09; N, 14.13. Found: C, 72.72; H, 5.30; N, 14.29.

Preparation of Compound 29—N-[4-(Phenylsulfonyl)benzyl]-N-methyl-6-aminobenz[cd]indol-2(1H)-one]

To a rapidly stirred solution of 60 mg (0.32 mmol) of the amine (28) and 78 μl (0.45 mmol) of diisopropylethylamine in 2 ml of DMF at 90° C. was added 120 mg (0.39 mmol) of 4-bromomethyldiphenylsulfone (7). After 2 hours, an additional 24 mg (0.08 mmol) of the bromide along with 17 μl (0.09 mmol) of base were added. After two hours, the mixture was poured into 1:1 $H_2O$/saturated $NaHCO_3$ (40 ml), and the aqueous layer was extracted with EtOAc (3×60 ml). Each organic layer was washed with $H_2O$ (2×20 ml). The combined organic layers were dried (anhydrous $Na_2SO_4$), and the solvent was removed under reduced pressure. The crude residue was chromatographed on flash silica gel (20 g) with EtOAc/$CH_2Cl_2$ (15:85). In this manner, there was obtained 130 mg (95%) of the desired product as an orange solid: m.p. 228°–230° C. (EtOAc); IR (KBr) 1670, 1470, 1450, 1310, 1150, 725 $cm^{-1}$; $^1H$ NMR (CDCl$_3$), δ 2.80 (s,3H,—NCH$_3$), 4.39 (s,2H,—NCH$_2$Ar), 6.83 (d,1H, J=7.6 Hz), 6.88 (d,1H,J=7.6 Hz), 7.50–7.61 (m,5H), 7.68 (t,1H,J=7.33 Hz), 7.75 (brs,1H,—NHC—O, 7.94 (d,2H,J= 8.5 Hz), 7.97 (d,2H,J=7.3 Hz), 8.08 (d,1H,J=7.0 Hz), and 8.19 (d,1H,J=8.3 Hz). Anal. Calcd. for $C_{25}H_{20}O_3N_2S$: C, 70.07; H, 4.70; N, 6.54; S, 7.48. Found: C, 70.32; H, 4.72; N, 6.37; S, 7.22. High Res. Mass Spec. Calcd. for $C_{25}H_{20}O_3N_2S$: 428.1195. Found: 428.1181.

Example 9

Preparation of Compounds 30 and 31

Compounds 30 and 31 were prepared in accordance with the following reaction scheme:

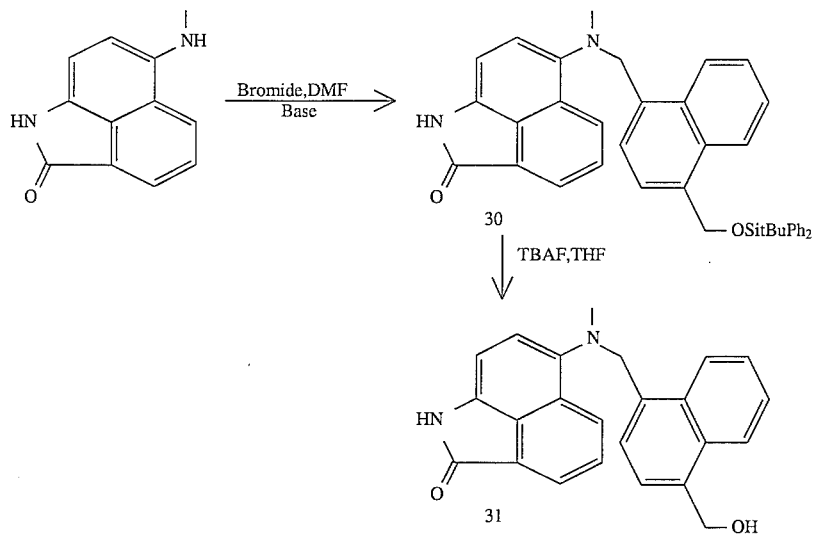

Preparation of Compound 30—N-[4-(tert-Butyldiphenylsilyl)oxymethyl-1-naphthobenzyl]-N-methyl-6-aminobenz[cd]indol-2(1H)-one To a rapidly stirred solution of 165 mg (0.83 mmol) of N-methyl-6-aminobenz[cd]indol-2(1H)-one (28) and 194 μl (1.10 mmol) of diisopropylethylamine in 5 ml of DMF at 100° C. was added 400 mg (1.10 mmol) of 1-bromomethyl-4-[(tert-butyldiphenylsilyl)oxy]methylnaphthalene. After three hours, the mixture was poured into 1:1 $H_2O$/saturated $NaHCO_3$ (100 ml), and the aqueous layer was extracted with ethyl acetate (2×100 ml). Each organic layer was washed with $H_2O$ (2×50 ml), and the combined organic layers were dried (anhydrous $Na_2SO_4$). The solvent was removed under reduced pressure, and the crude residue was chromatographed on flash silica gel (20 g) with EtOAc/$CH_2Cl_2$ (15:85). In this manner, there was obtained 417 mg (83%) of the desired material as an orange foam: IR (KBr) 3180, 3040, 2930, 2850, 1620, 1350, 1220, 1070, 1030, 735 $cm^{-1}$; $^1H$ NMR ($CDCl_3$) δ 112 (s,9H), 2.92 (s,3H,—N—$CH_3$) 4.81 (s,2H,—$NCH_2Ar$), 5.26 (s,2H,—$OCH_2Ar$), 6.92 (d,1H,J=7.5 Hz), 7.05 (d,1H,J=7.5 Hz), 7.35–7.5 (m,8H), 7.60 (t,1H,J=7.1 Hz), 7.68–7.82 (m,6H), 7.95 (m,2H), 8.06 (m,2H), and 8.19 (d,1H,J=8.3 Hz). High Res. Mass Spec. Calcd for $C_{40}H_{38}N_2O_2Si$: 606.2703. Found: 606.2720.

Preparation of Compound 31—N-[4-Hydroxymethyl-1-naphthobenzyl]-N-methyl-6-aminobenz[cd]indol-2(1H)-one To a rapidly stirred solution of 412 mg (0.68 mmol) of the silyl ether (30) in 6 ml of THF at 25° C. was added 1.2 ml (1.36 mmol) of a 1.1M solution of tetra-n-butylammonium-fluoride in THF. After 10 minutes, the mixture was poured into $H_2O$ (50 ml), and the aqueous layer was extracted with ethyl acetate (3×100 ml). Each organic layer was washed with $H_2O$ (40 ml), and the combined organic layers were dried (anhydrous $Na_2SO_4$). The solvent was removed under reduced pressure. In this manner, there was obtained 212 mg (85%) of the desired product as an orange solid: m.p. 230°–232° C.; IR (KBr) 3380, 3160, 2820, 1620, 1435, 1395, 1340, 1225, 1195, 1070, 920, 815, 740 $cm^{-1}$; $^1H$ NMR ($D_6DMSO$) δ 2.85 (s,3H,—$NCH_3$) 4.76 (s,2H,—$NCH_2Ar$), 4.94 (d,2H,J=5.2 Hz,$ArCH_2O$—), 5.28 (t,1H,J=5.2 Hz,—OH), 6.87 (d,1H,J=7 Hz), 7.11 (d,1H,J=7.5 Hz), 7.42–7.57 (m,3H), 7.62–7.75 (m,2H), 7.94 (d,1H,7.0 Hz), 8.06–8.18 (m,3H), 10.61 (s,1H,—NHC=O). Anal. Calcd. for $(C_{24}H_{20}N_2)_2$: C, 78.24; H, 5.47; N, 7.60. Found: C, 77.97; H, 5.53; N, 7.51.

Example 10

Preparation of Compounds 32 through 34

Compounds 32 through 34 are prepared in accordance with the following reaction scheme:

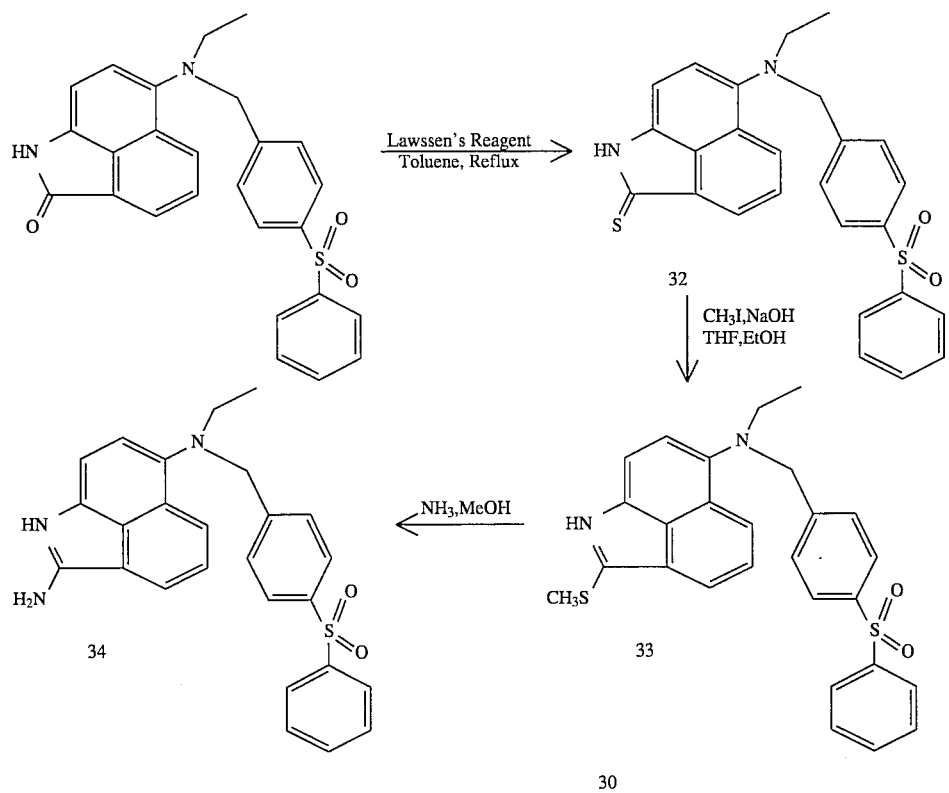

Preparation of Compound 32—N-[4-(Phenylsulfonyl)benzyl]-N-ethyl-6-aminobenz[cd]indol-2(1H)-thione To a rapidly stirred solution of 200 mg (0.45 mmol), of the lactam N-[4-(phenylsulfonyl)benzyl]-N-ethyl-6-aminobenz[cd]indol-2(1H)-one (8) in 10 ml of toluene at 110° C. was added mg (0.49 mmol) of Lawssen's reagent. After one hour, the solvent was removed under reduced pressure, and the crude residue was chromatographed on flash silica gel (30 g) with Et$_2$O/CH$_2$Cl$_2$ 3:97). In this manner, there was obtained 198 mg (96%) of the desired thiolactam as a red glass: IR (KBr) 3300, 3060, 1420, 1290, 1140, 810, 720 cm$^{-1}$; $^1$H NMR (CDCl$_3$) δ 1.12 (t,3H,J=7 Hz), 4.37 (q,2H,J=7 Hz), 4.45 (s,2H,—NCH$_2$Ar), 6.85 (d,1H,J=7.7 Hz), 6.94 (d,1H, J=7.7 Hz), 7.46–7.60 (m,5H), 7.68 (t,1H,J=7.4 Hz), 7.88 (d,2H,J=8.3 Hz), 7.95 (d,2H,J=6.3 Hz), 8.26 (m,2H), and 9.27 (brs,1H,—NHC=S). High Res. Mass Spec. Calcd. for C$_{26}$H$_{22}$N$_2$O$_2$S$_2$: 458.1123. Found: 458.1130.

Preparation of Compound 33—N-[4-(Phenylsulfonyl)benzyl]-N-ethyl-6-aminobenz[cd]indol-2-thiomethyl To a rapidly stirred solution of 190 mg (0.41 mmol) of the thiolactam (32) and 0.91 ml (0.91 mmol ) of an aqueous 1N NcOH solution in 4 ml of a 3:1 EtOH/THF mixture at 25° C. was added 28 μl (0.46 mmol) of methyl iodide. After 2 hours, the mixture was poured into H$_2$O (50 ml), and the aqueous was extracted with ethyl acetate (3×100 ml). The combined organic layers were dried (anhydrous Na$_2$SO$_4$), and the solvent was removed under reduced pressure. The crude residue was chromatographed on flash silica gel (20 g) with EtOAc/CH$_2$Cl$_2$ (5:95). In this manner, there was obtained 172 mg (88%) of the desired material as a red solid: m.p. 182°–184° C. (EtOAc); IR (KBr) 2920, 1435, 1300, 1225, 1150, 725 cm$^{-1}$; $^1$H NMR (CDCl$_3$) δ 1.15 (t,3H,J=7.1 Hz), 2.83 (s,3H,—SCH$_3$), 3.33 (q,2H,J=7.1 Hz), 4.52 (s,2H, —NCH$_2$Ar), 6.84 (d,1H,J=7.6 Hz), 7.45 (d,1H,J=7.6 Hz), 7.50–7.60 (m,6H), 7.82–7.95 (m,5H), and 8.11 (d,1H,J=8.1 Hz). Anal. Calcd. for C$_{27}$H$_{24}$N$_2$O$_2$S$_2$: C, 68.61; H, 5.12; N, 5.93; S, 13.57. Found: C, 68.83; H, 5.12; N, 5.80; S, 13.32.

Preparation of Compound 34—N-[4-(Phenylsulfonyl)benzyl]-N-ethyl-6-aminobenz[cd]indol-2-amine A mixture of 20 mg (0.04 mmol) of the thiomethyl ether (33) in 1 ml of MeOH saturated with ammonia was heated in a sealed tube at 160° C. for 4 hours. After cooling, the solvent was removed under reduced pressure and the crude residue was chromatographed on flash silica gel (15 g) with a gradient of –10% MeOH/CH$_2$Cl$_2$. In this manner, there was obtained 18 mg (96%) of the desired amidine as a red foam: IR (KBr) 2690, 1620, 1430, 1300, 1140, 1100, 720 cm$^{-1}$; $^1$H NMR (CDCl$_3$) δ 1.07 (t,3H,J=7.0 HZ), 3.21 (q,2H,J=7.0 Hz), 4.40 (s,2H,—NCH$_2$Ar), 6.84 (d,1H,J=7.7 HZ), 7.10 (d,1H,J=7.7 HZ), 7.45–7.55 (m,5H), 7.61 (t,1H, J=7.8 Hz), 7.82–7.95 (m,4H), 8.21 (d,1H,J=8.2 Hz), 8.25 (brs,2H,—NH$_2$), and 8.54 (d,1H,J=7.1 Hz). High Res. Mass Spec. Calcd. for C$_{26}$H$_{23}$N$_3$O$_2$S: 441.1511. Found: 441.1515.

Example 11

Preparation of Compounds 35 through 37

Compounds 35 through 37 were prepared in accordance with the following reaction scheme:

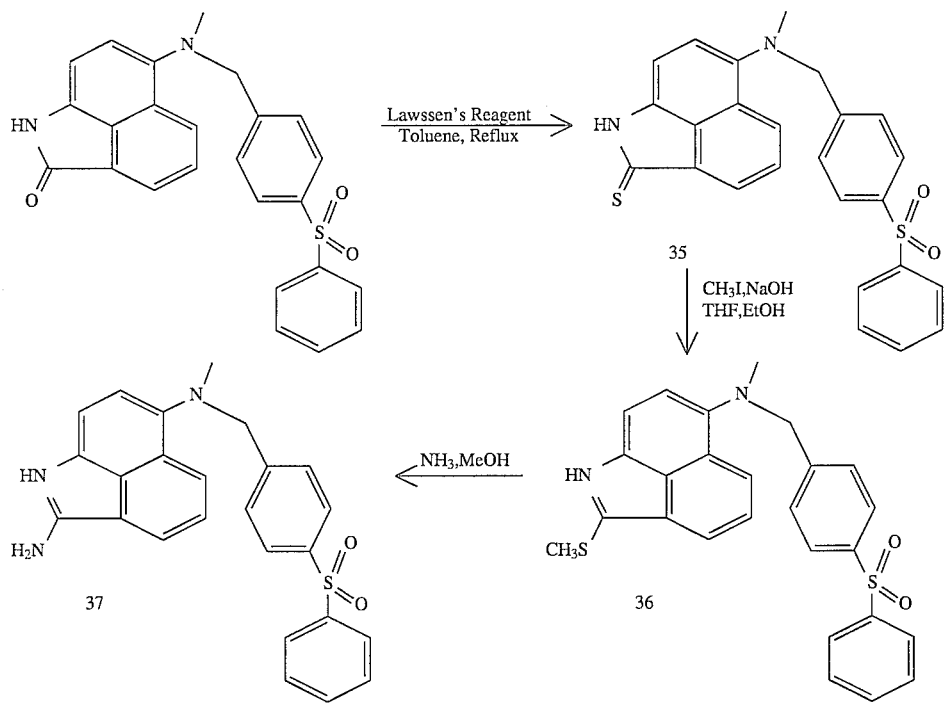

Preparation of Compound 35—N-[4-(Phenylsulfonyl)benzyl]-N-methyl-6-aminobenz[cd]indol-2(1H)-thione To a rapidly stirred solution of 547 mg (1.28 mmol) of N-[4-(phenylsulfonyl)benzyl]-N-methyl-6-aminobenz[cd]indol-2(1H)-one (29) in 30 ml of toluene at 120° C. was added 568 mg (1.40 mmol) of Lawssen's reagent. After one hour, the solvent was removed under reduced pressure, and the crude residue was chromatographed on flash silica gel (50 g) with $Et_2O/CH_2Cl_2$ (4:96). In this manner, there was obtained 268 mg (47%) of the desired material as a red solid: m.p. 196°–199° C.; IR (KBr) 3160, 1430, 1415, 1300, 1180, 1145, 1100, 925, 805, 725 cm$^{-1}$; $^1$H NMR (CDCL$_3$) δ 2.84 (s,3H,—NCH$_3$), 4.47 (S,2H,—NCH$_2$Ar), 6.85 (d,1H,J=7.7 Hz), 6.98 (d,1H,J=7.7 Hz), 7.49–7.61 (m,5H), 7.66 (t,1H, J=7.3 Hz), 7.93–8.01 (m,4H), 8.19 (d,1H,J=8.1 Hz), 8.25 (d,1H,J=7.3 Hz), and 9.32 (brs,1H,—NHC=S). High Res. Mass Spec. Calcd. for $C_{25}H_{20}N_2O_2S_2$: 444.0966. Found: 444.0963.

Preparation of Compound 36—N-[4-(Phenylsulfonyl)benzyl]-N-methyl-6-aminobenz[cd]indol-2-thiomethyl To a rapidly stirred solution of 265 mg (0.60 mmol) of the thiolactam (35) and 1.3 ml (1.31 mmol) of a 1N aqueous NaOH solution in 10 ml of 1:1 EtOH/THF at 25° C. was added 41 μl (0.66 mmol) of methyl iodide. After 30 minutes, the mixture was poured into H$_2$O (50 ml), and the aqueous layer was extracted with ethyl acetate (3×60 ml). The combined organic layers were dried (anhydrous Na$_2$SO$_4$), and the solvent was removed under reduced pressure. The crude residue was chromatographed on flash silica gel (30 g) with EtOAc/CH$_2$Cl$_2$ (1:9). In this manner, there was obtained 259 mg (95%) of the desired material as a red solid: m.p. 209° C.; IR (KBr) 2800, 1410, 1300, 1200, 1145, 1100, 920, 810, 770, 720 cm$^{-1}$; $^1$H NMR (CDCl$_3$) δ 2.84 (s,3H), 2.89 (s,3H), 4.57 (s,2H,—NCH$_2$Ar), 6.84 (d,1H,J=7.6 Hz), 7.48–7.62 (m,7H), 7.85 (d,1H,J=7.0 Hz), 7.93–8.00 (m,4H), and 8.03 (d,1H,J=8.1 Hz). High Res. Mass Spec. Calcd. for $C_{26}H_{22}N_2O_2S_2$: 458.1123. Found: 458.1107.

Preparation of Compound 37—N-[4-(Phenylsulfonyl)benzyl]-N-methyl-6-aminobenz[cd]indol-2-amine A mixture of 255 mg (0.56 mmol) of the thiomethylether (36) in 10 ml of MeOH saturated with ammonia was heated in a sealed tube to 145° C. for 5 hours. After cooling, the solvent was removed under reduced pressure, and the crude residue was chromatographed on flash silica gel (30 g) with MeOH/CH$_2$Cl$_2$ (1:9). In this manner, there was obtained 207 mg (87%) of the desired amidine as a red foam: IR (KBR) 2840, 1610, 1410, 1295, 1215, 1140, 1090, 1050, 805, 720 cm$^{-1}$; $^1$H NMR (D$_6$DMSO) δ 2.83 (s,3H,—N—CH$_3$), 4.46 (s,2H,—NCH$_2$Ar), 6.86 (d,1H,J=7.6 Hz), 7.16 (d,1H,J=7.6 Hz), 7.49–7.61 (M,5H), 7.66 (t,1H,J=8.1 Hz), 7.92–8.02 (m,Hz), 820 (d,1H,J=8.2 Hz), and 8.55 (d,1H,J=7.2 Hz). High Res. Mass Spec. Calcd. for $C_{25}H_{21}N_3O_2S$: 427.1354. Found: 427.1370.

Example 12

Preparation of Compounds 38 through 40

Compounds 38 through 40 are prepared in accordance with the following reaction scheme:

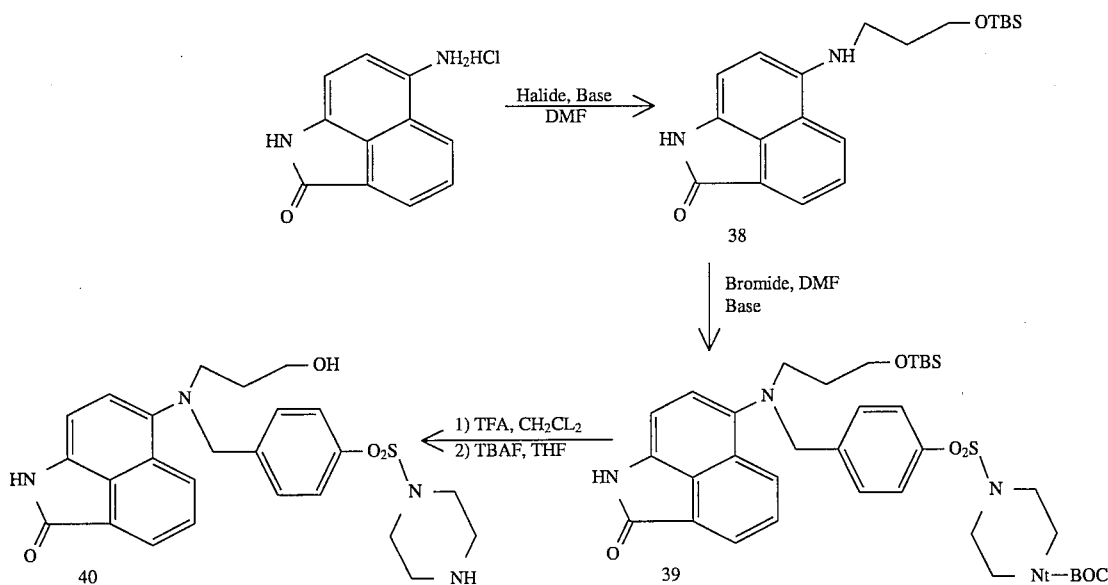

Preparation of Compound 38—N-[3(1-t-Butyldimethylsiloxypropyl] 6-aminobenz[cd]indol-2(1H)-one A stirred solution of 0.613 g (2.76 mmol) 6-aminobenz[cd]indol-2(1H)-one hydrochloride (2) in 10 ml of DMF were added to 1.1 ml (6.31 mmol) of N,N-diisopropylethylamine (DIEA) and 0.778 g (3.07 mmol) of 3-bromopropyl-1-t-butyl-dimethyl silyl ether. The resulting mixture was heated at 120° C. for 4 hours after which 0.15 g (0.59 mmol) of bromide and 0.10 ml (0.57 mmol) DIEA were added. After heating for 24 hours, the reaction mixture was cooled and poured into 100 ml of $H_2O$ and extracted with $CH_2Cl_2$ (2×200 ml). The organic layers were combined, dried (anhydrous $MgSO_4$) and, after removal of the solvent at reduced pressure, the crude residue was flash chromagraphed on silica gel with hexane-ethyl acetate (1:1). In this manner, there was obtained 0.45 g (46%) of the desired product (38) as a red solid: m.p. 126°–129° C.; IR (KBr) 3400, 3200, 2920, 2880, 1680, 1630 cm$^{-1}$; $^1$H NMR (CDCl$_3$) δ 0.10 (s,6H), 0.93 (s,9H), 2.00 (m,2H), 3.38 (m,2H), 3.86 (t,2H, J=5.5 Hz), 4.93 (bs,1H), 6.37 (d,1H,J=7.7 Hz), 6.84 (d,1H, J=7.7 Hz), 7.67 (t,1H,J=7.2 Hz), 8.00 (bs,1H), 8.01 (d,1H, J=7.1 Hz), and 8.09 (d,1H,J=7.1 Hz). Anal. Calcd. for $C_{20}H_{28}N_2O_2Si$ (exact mass): 356.1921. Found: 356.1920.

Preparation of Compound 39—N-[3(1-t-Butyldimethyl-siloxypropyl)amino-4-methylphenylsulfonyl-t-butyl-1-1-piperazinecarboxylate-6-aminobenz[cd]indol-2(1H)-one A stirred solution of 0.242 g (0.68 mmol) aniline (38), 0.300 g (0.72 mmol) bromide (12) and 0.13 ml (0.72 mmol) of DIEA was heated to 100° C. for 4 hours. At that time, another 0.03 g (0.07 mmol) bromide and 0.012 ml (0.07 mmol) DIEA were added. After 1.5 hours, the reaction mixture was cooled and poured into 50 ml saturated aqueous NaCl. The precipitate was collected, dried in vacuo and flash chromatographed on silica, eluting with hexane-ethyl acetate (1:1). In this manner, there was obtained 0.430 g (91%) of the desired product (39) as an orange brittle foam: IR (KBr) 2920, 2860, 1675, 1160 cm$^{-1}$; $^1$H (CDCl$_3$) δ −0.05 (s,6H), 1.40 (s,9H), 1.78 (m,2H), 2.94 (t,4H,J=5.0 Hz), 3.28 (t,2H,J=7.3 Hz), 3.49 (t,4H,J=5.0 Hz), 3.60 (t,2H,J=5.9 Hz), 4.43 (s,2H), 6.80 (d,1H,J=7.6 Hz), 6.90 (d,1H,J=7.6 Hz), 7.49 (d,2H,J=8.3 Hz), 7.65 (d,2H,J=8.3 Hz), 7.72 (t,1H,J= 7.1 Hz), 8.01 (bs,1H), 8.08 (d,1H,J=7.0 Hz), and 8.29 (d,1H,J=8.2 Hz). Anal. Calcd. for $C_{36}H_{50}N_4O_6SiS$ (exact mass): 694.3223. Found: 694.3244.

Preparation of Compound 40—N-[4-(N,N-Piperazinylsulfamoyl)benzyl]-N-hydroxypropyl-6-aminobenz[cd]indol-2-(1H)-one 0.6 ml of trifluoroacetic acid (TFA) were added to a stirred solution of 0.343 g (0.49 mmol) of (39) in 5 ml of $CH_2Cl_2$. After 2.5 hours, the volatiles were removed at reduced pressure, and the orange oily residue was dissolved in 5 ml THF. 0.5 ml of a 1M solution of tetrabutylammonium fluoride in THF (0.50 mmol) were added. After two hours at room temperature, the reaction mixture was poured into 50 ml $H_2O$ and extracted repeatedly with ethyl acetate until the aqueous layer was colorless. The combined organic layers were dried (anhydrous $MgSO_4$) and, after removal of the solvent, the crude residue was flash chromatographed on silica, eluting first with EtOAc-MeOH (0–15%) and then with EtOAc-MeOH—$CH_3CN$ (8:1:1). Appropriate fractions were collected, concentrated, dissolved in 300 ml ethyl acetate and washed with 4×150 ml $H_2O$ to remove tetrabutylammonium salts which co-eluted with the product (3). The ethyl acetate layer was dried (anhydrous $MgSO_4$) and, after removal of the solvent, the solid was recrystallized from $CH_3CN$. In this manner, 0.13 g (55%) of (40) was obtained as a yellow solid: m.p. 178°–179° C.; IR (KBr) broad 3300, 1680, 1450, 1350, 1160 cm$^{-1}$; $^1$H (CDCl$_3$) δ 1.81 (m,2H), 2.92 (m,8H), 3.28 (t,2H,J=6.8 Hz), 3.69 (t,2H, J=6.04 Hz), 4.42 (s,2H), 6.84 (d,1H,J=7.5 Hz), 6.95 (d,1H, J=7.6 Hz), 7.47 (d,2H,J=8.3 Hz), 7.67 (d,2H,J=8.3 Hz), 7.75 (t,1H,J=7.1 Hz), 7.83 (bs,1H), 8.09 (d,1H,J=6.9 Hz), and 8.29 (d,1H,J=8.3 Hz). Anal. calcd. for $C_{25}H_{28}N_4O_4S$ (exact mass): 480.1833. Found: 480.1850.

Example 13

Preparation of Compound 41

Compound 41 was prepared in according with the following reaction scheme:

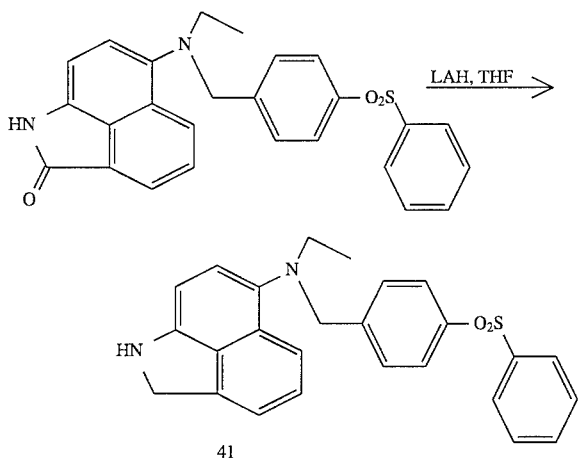

Preparation of Compound 41—N-[4-(phenylsulfonyl)benzyl]-N-ethyl-6-amino-dihydrobenz[cd]indole 152 mg (0.34 mmol) N-[4-(phenylsulfonyl)benzyl]-N-ethyl-6aminobenz[cd]indol-2(1H)one (8) in 5 ml of dry THF was added via syringe to a suspension of 28 mg (0.74 mmol) of LAH (i.e., lithium aluminum anhydride) in 5 ml THF. The reaction mixture was allowed to stir under an argon atmosphere at room temperature for 1.5 hours, after which the reaction mixture was quenched with saturated aqueous $NaHCO_3$ (15 ml) and extracted with 2×25 ml ethyl acetate. The organic layers were dried over anhydrous $MgSO_4$ and concentrated at reduced pressure. The resulting dark colored film was chromatographed on gravity silica gel, eluting with degassed $CH_2Cl_2$ under medium $N_2$ pressure. In this manner, there was obtained 46 mg (31%) of (41) as a lightly colored brittle foam which decomposed slowly upon exposure to air. $^1H$ NMR ($CDCl_3$) δ 1.00 (t,2H,J=7.0 Hz), 3.05 (q,2H,J=7.0 Hz), 4.25 (s,2H), 4.88 (s,2H), 6.32 (d,1H,J=7.6 Hz), 6.86 (d,1H,J=7.6 Hz), 7.18 (d,1H,J=6.8 Hz), 7.40–7.54 (m,6H), 7.76 (d,1H,J=8.4 Hz), 7.83 (d,2H,J=8.3 Hz), and 7.92 (dd,2H,J=8.3 Hz, 1.5 Hz).

Example 14

Preparation of Compounds 42 through 47

Compounds 42 through 47 were prepared in accordance with the following reaction scheme:

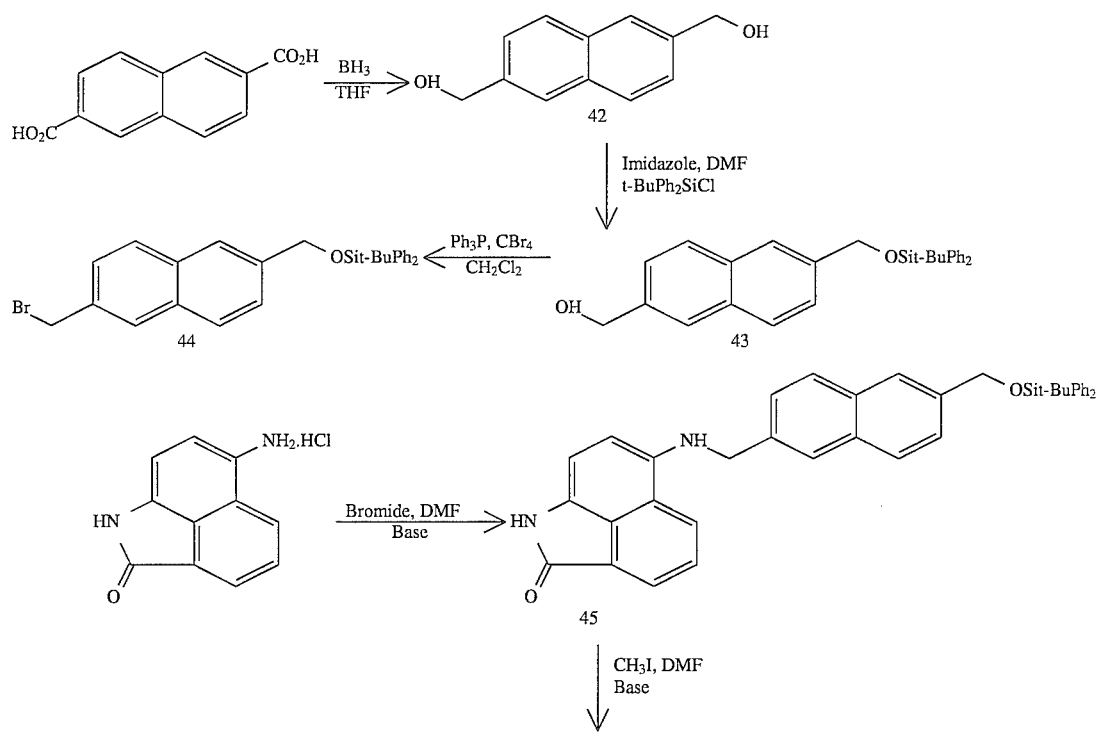

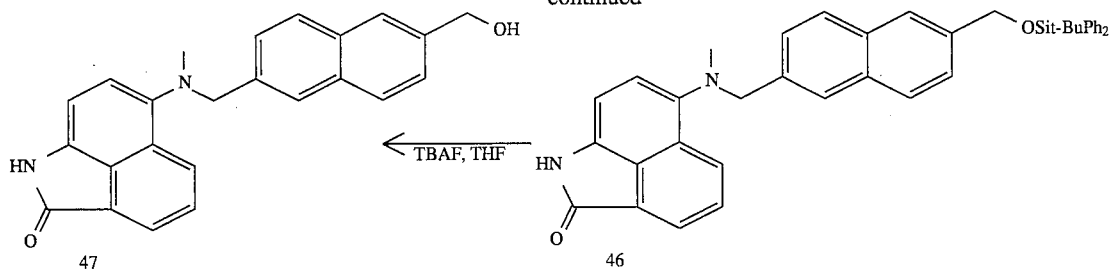

Preparation of Compound 42—2,6-Hydroxymethylnaphthalene 102 ml (102 mmol) of 1M solution of BH₃.THF in THF was placed in a dropping funnel and slowly added to a suspension of 10.0 g (46.25 mmol) of 2,6-naphthalenedicarboxylic acid in 130 ml THF cooled to 0° C. When the addition was complete, the reaction mixture was warmed to room temperature and stirred for 18 hours and then quenched with H₂O. The aqueous layer was saturated with K₂CO₃, and the layers separated. The aqueous layer was extracted again with ethyl acetate. The combined organic layers were washed with brine, dried (anhydrous MgSO₄) and concentrated at reduced pressure. In this manner, there was obtained 7.37 g (85%) of (42). An analytical sample was crystallized from THF: m.p. 172°–173° C.; IR (KBr) 3200 (broad), 1020, 890, 820 cm⁻¹; ¹H NMR (dmso-d₆) δ 4.63 (d,4H,J=5.6 Hz), 5.30 (t,2H,J=5.6 Hz), 7.43 (dd,2H,J=8.5, 1.0 Hz), 7.77 (s,2H), and 7.82 (D,2H,J=8.4 Hz). Anal. Calcd. for C₁₂H₁₂O₂: C, 76.57; H, 6.43. Found: C, 76.77; H, 6.48.

Preparation of Compound 43—2-Hydroxymethyl-6-tert-butyldiphenylsiloxymethylnaphthalene 7.37 g (39.16 mmmol) of diol (42) was dissolved in 40 ml DMF. 2.66 g (39.20 mmol) of imidazole and 10.2 ml (39.16 mmol) of tert-butyldiphenyl-chlorosilane were added and allowed to stir overnight. Volatiles were removed at reduced pressure and the residue dissolved in 250 ml ethyl acetate and washed with 0.5N HCl. The organic layer was dried (anhydrous MgSO₄) and concentrated. The crude oil was chromatographed on flash silica, eluting with CH₂Cl₂. In this manner, 9.8 g (59%) of the monoprotected diol (43) was obtained as a colorless oil. ¹H NMR (CDCL₃) δ 1.12 (S,9H), 1.77 (t,1H,J=6.0 Hz), 4.85 (d,2H,J=6.0 Hz), 4.92 (s,2H), 7.34–7.48 (m,8H), and 7.70–7.83 (m,8H).

Preparation of Compound 44—2-Bromomethyl-6-tert-butyldiphenylsiloxymethylnaphthalene 4.31 g (16.40 mmol) of triphenylphosphine was dissolved in 20 ml CH₂Cl₂ and cooled to 0° c. 2.72 g (8.2 mmol) of carbon tetrabromide was added. After 5 minutes, 3.50 g (8.20 mmol) of the alcohol (43) dissolved in 10 ml CH₂Cl₂ was added. Reaction was completed in 10 minutes, after which the volatiles were evaporated at reduced pressure. The crude oily residue was filtered through a short column of silica, eluting with CH₂Cl₂, to remove triphenylphosphine oxide. In this manner, there was obtained 2.80 g (68%) of the bromide product as an oil, which was used in subsequent reactions without further purification. ¹H NMR (CDCl₃) δ 1.12 (s,9H), 4.64 (s,2H), 4.91 (s,2H), 7.37–7.43 (m,8H), and 7.70–7.81 (m,8H). Anal. Calcd. for C₂₈H₂₉BrOS (exact mass): 488.1171 Found: 488.1157.

Preparation of Compound 45—N-[2-Methyl-6-tert-butyldiphenylsiloxymethylnaphthalene] 6-aminobenz[cd]indol-2(1H)-one The amine (45) was prepared in similar fashion to (38) above using 2-bromomethyl-6-tert-butyldiphenyl-siloxymethylnaphthalene. After work up, the crude residue was chromatographed, eluting with CH₂Cl₂:EtOAc (5:1). In this manner, there was obtained (45) in yield as an orange solid: m.p. 182°–184° C.; IR (KBr) 2915, 2830, 1700, 1450, 1100 cm⁻¹; ¹H NMR (CDCl₃) δ 1.12 (s,9H), 4.64 (s,2H), 4.80 (bs,1H), 4.92 (s,2H), 6.45 (d,1H,J=7.7 Hz), 6.79 (d,1H,J=7.6 Hz), 7.36–7.87 (m,18H), 8.08 (d,1H,J=8.1 Hz), and 8.11 (d,1H,J=7.1 Hz). Anal. Calcd. for C₃₉H₃₆N₆O₂Si (exact mass): 592.2548. Found: 592.2562.

Preparation of Compound 46—N-[2-Methyl-6-tert-butyldiphenylsiloxymethylnaphthalene]-N-methyl-6-aminobenz[cd]indol-2-(1H) -one A solution of 823 mg (1.39 mmol ) of amine (45), 0.25 ml (1.44 mmol) DIEA, and 0.091 ml (1.46 mmol) of iodomethane in 15 ml DMF was heated to 75° C. for 3 hours. At that time, 0.086 ml (1.39 mmol) of CH₃I and 0.24 ml (1.39 mmol) DIEA were added. Heating was continued for 12 hours. The crude mixture was poured into 50 ml cold H₂O. The precipitate was filtered, dried in vacuo and chromatographed on silica gel, eluting with CH₂Cl₂-EtOAc (10:1). In this manner, there was obtained 300 mg (36%) of (46) as an orange solid. IR (KBr) 2925, 1680, 1460, 1000, 810 cm⁻¹; ¹H NMR (CDCl₃) 1.12 (s,9H), 2.87 (s,3H), 4.54 (s,2H), 4.93 (s,2H), 6.86 (d,1H,J=7.6 Hz), 6.92 (d,1H,J=7.6 Hz), 7.36–7.84 (m,17H), 7.90 (bs,1H), 8.09 (d,1H,J=7.0 Hz), and 8.37 (d,1H,J=8.2 Hz). Anal. Calc for C₄₀H₃₈N₂O₂Si (exact mass): 606.2704 Found: 606.2707.

Preparation of Compound 47—N-(6-Hydroxymethyl-2-naphthobenzyl)-N-methyl-6-aminobenz[cd]indol-2(1H)-one To a stirred solution of 288 mg (0.47 mmol) of amine (46) in 5 ml of THF was added 0.65 ml (0.71 mmol) of a 1.1M solution of tetra-n-butyl ammonia fluoride in THF. After 10 minutes, the reaction mixture was diluted with 10 ml H₂O and extracted with ethyl acetate until the orange precipitate was dissolved. The organic layers were combined and washed with 20 ml saturated aqueous NaCl and dried (anhydrous MgSO₄). The solvent was then removed at reduced pressure. The remaining orange solid was refluxed with 10 ml ethyl acetate, cooled and filtered. This last procedure was then repeated. In this manner, there was obtained 125 mg (69%) of (47) as an orange solid: m.p. 205°–206° C. (decomp.); IR (KBr) 3350, 3160, 1710, 1450, 1200 cm⁻¹; ¹H NMR (DMSO-D₆) δ 2.78 (s,3H), 4.47 (s,2H), 4.64 (s,2H), 6.84 (d,1H,J=7.5 Hz), 6.97 (d,1H,J=7.6

Hz), 7.44 (dd,1H,J=8.5, 1.3 Hz), 7.51 (dd,1H,J=8.5, 1.3 Hz), 7.75–7.89 (m,5H), 7.98 (d,1H,J=6.9 Hz), 8.33 (d,1H,J=8.2 Hz), and 10.62 (s,1H). Anal. calcd. for $C_{24}H_{20}N_2O_2$ (exact mass): 368.1526. Found: 368.1525.

Example 15

Preparation of Compounds 48 and 49

Compounds 48 and 49 were prepared by the following reaction scheme:

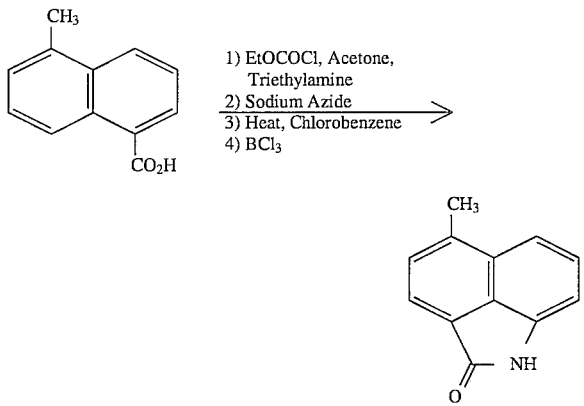

Preparation of Compound 48—5-Methylnaphthylacylazide

To a rapidly stirred solution of 1.023 ml (10.7 mmol) of ethyl chloroformate in 10 ml of acetone at −5° C. was added a solution of 1.00 g (5.37 mmol) 5-methylnaphthoic acid and 1.50 ml (10.7 mmol) triethylamine in 15 ml of acetone dropwise over 10 minutes. After stirring at −5° C. for 30 minutes, a solution of 0.696 g (10.7 mmol) sodium azide in 10 ml of water was added dropwise to the mixture. After stirring at −5° C. for 30 minutes, the resulting slurry was poured into 100 ml of water. The product was collected by filtration as a white solid (0.934 g, 82%) and was used without further purification: m.p. 69°–70° C. (decomp.); $^1$H NMR (CDCl$_3$) δ 2.73 (s,3H), 7.40 (d,1H,J=7.0 Hz), 7.50–7.57 (m,2H), 8.23–8.31 (m,2H), and 8.92 (d,1H,J=8.6 Hz).

Preparation of Compound 49—5-Methylnaphthostyril

To a pot of 25 ml of dry distilling chlorobenzene under argon was added dropwise a solution of 100 mg (0.54 mmol) of 5-methylnaphthylacylazide (dried by azeotroping with benzene) in 2 ml of dry chlorobenzene. The solvent was distilled over a one hour period to an approximately 1 ml volume.

The resulting isocyanate solution was added to a tube containing approximately 4 ml condensed boron trichloride at −78° C. The tube was sealed and heated at 110°–120° C. with stirring for 85 hours. After cooling to ambient temperature, the tube was opened and boron trichloride was allowed to escape. The dark solution was poured into 50 ml 0.5N HCl. The tube was rinsed with ethyl acetate (2×5 ml) and THF (2×5 ml). The aqueous solution was extracted with ethyl acetate (2×20 ml) and CH$_2$Cl$_2$ (2×20 ml). The combined extracts were washed with brine (20 ml) and dried (anhydrous Na$_2$SO$_4$), and the solvent was removed under reduced pressure. The residue was chromatographed on flash silica gel (10 g) using THF/CH$_2$Cl$_2$ (5:95) as the eluent. In this manner, there was obtained 25 mg (25%) of the desired material as a yellow solid: m.p. 215°–217° C.; $^1$H NMR (CDCl$_3$) δ 6.96 (d,1H,J=7.03 Hz), 7.46 (m,dd,1H,J$_1$=7.13 Hz, J$_2$=8.55 Hz), 7.53 (d,1H,J=7.06 Hz), 7.64 (d,1H, J=8.5 Hz), 7.83 (broad s,1H), and 7.98 (d,1H,J=7.1 Hz); IR (KBr) 3195, 1685, 1640, 1495, 765 cm$^{-1}$. Anal. calculated for $C_{12}H_9NO$: C, 78.67; H, 4.95; N, 7.65. Found: C, 78.40; H, 4.99; N, 7.57.

Example 16

Preparation of Compounds 50 through 53

Compounds 50 through 53 were prepared according to the following reaction scheme:

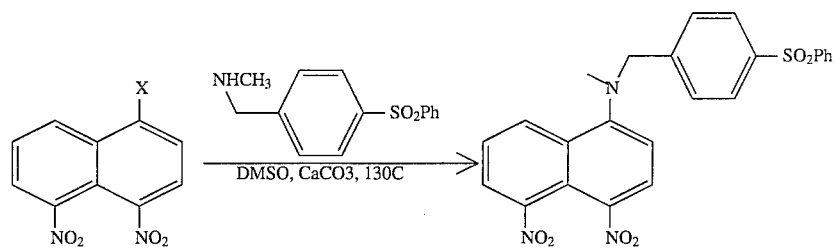

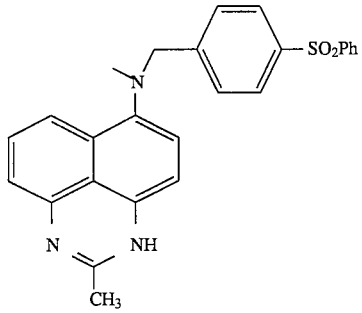

Preparation of Compound 50—4-[Methylaminomethyl]diphenylsulfone

A solution of 5.02 g (16.14 mmol) of 4-bromomethyl-diphenylsulfone in 100 ml THF was slowly added over a one hour period to a rapidly stirred solution of 14.0 ml (162.63 mmol) of 40% by weight aqueous methylamine in 50 ml THF. The mixture was then concentrated under reduced pressure to 30 ml, diluted with 100 ml $CH_2Cl_2$, and extracted with 2×120 ml 0.5N HCl. The combined aqueous layers were made basic with 6N NaOH and extracted with 2×150 ml $CH_2Cl_2$. The combined organic layers were dried (anhydrous $MgSO_4$), and the solvent was removed under reduced pressure. In this manner, there was obtained 2.30 g (55%) of the desired product as a white solid: m.p. 107°–110° C.; IR (KBr) 3340, 2840, 1450, 1400, 1300, 1150, 1100 $cm^{-1}$; NMR ($CDCl_3$) δ 2.42 (s,3H), 3.79 (s,2H), 7.45–7.60 (m,5H), and 7.88–7.95 (m,4H).

Preparation of Compound 51—N-[4-(Phenylsulfonyl)benzyl]-N-methyl-1-amino-4,5-dinitronaphthalene A stirred solution of 1.597 g (6.32 mmol) of 1-chloro-4,5-dinitronaphthalene, 1.650 g (6.32 mmol) of 4-[N-methylaminomethyl]diphenylsulfone and 0.82 g (8.19 mmol) of anhydrous calcium carbonate was stirred at 130° C. for 20 hrs. Another 0.150 g (0.57 mmol) of the amine was added and allowed to react for two more hours. The reaction mixture was cooled, poured into $H_2O$ (200 ml) and extracted with ethyl acetate (2×250 ml). The combined organic layers were dried (anhydrous $MgSO_4$), and the solvent was removed at reduced pressure. The crude residue was flash chromatographed on silica, eluting with $CH_2Cl_2$. In this manner, there was obtained 2.02 g (67%) of the desired product as an orange brittle foam. IR (KBr) broad 3420, 1560, 1520, 1340, 1310, 1150 $cm^{-1}$; NMR ($CDCl_3$) δ 2.91 (s,3H), 4.46 (s,2H), 7.15 (d,1H, J=8.5 Hz), 7.50–7.66 (m,7H), 7.97 (d,4H,J=8.0 Hz), 8.21–8.26 (m,2H), and 8.49 (d,1H,J=8.6 Hz). High Res. Mass Spec. Calcd. for $C_{24}H_{19}N_3O_6S$: 477.0996. Found: 477.1008.

Preparation of Compound 52—N-[4-(Phenylsulfonyl)benzyl]-N-methyl-4,5-diaminonaphthalene A stirred solution of 0.40 g (0.84 mmol) of N-[4-phenylsulfonyl)benzyl]-N-methyl-1-amino-4,5-dinitronaphthalene and 0.40 ml (8.25 mmol) of hydrazine monohydrate in 3 ml of 2:1 (THF:MeOH) solvent was brought to reflux. One drop of 50% Raney nickel in $H_2O$ was added. The color of the reaction mixture changed from red-brown to green. TLC indicated the reaction was complete. The reaction mixture was filtered through a diatomaceous earth material sold under the trade name Celite, and the solvent was removed under reduced pressure. The wet ($H_2O$) residue was dissolved in $CH_2Cl_2$ and dried over anhydrous $MgSO_4$. The solvent was removed under reduced pressure, and the crude residue was flash chromatographed, eluting with $CH_2Cl_2$: EtOAc (20:1). In this manner, there was obtained 137 mg (40%) of the diaminonaphthalene as a brown foam which rapidly decomposes. NMR ($CDCl_3$) δ 2.63 (s,3H), 4.15 (s,2H), 4.52 (bs,4H), 6.51 (d,1H,J=7.9 Hz), 6.62 (d,1H,J=6.85 HZ), 6.87 (d,1H,J=7.9 Hz), 7.21 (t,1H,J=7.9 Hz), 7.47–7.55 (m,5H), 7.87 (d,1H,J=8.2 Hz), 7.88 (d,2H,J=8.3 Hz), and 7.93–7.96 (m,2H). This material was used without delay in the cyclization step to make Compound 53.

Preparation of Compound 53—N-[4-(Phenylsulfonyl)benzyl]-N-methyl-4-amino-2-methylperimidine A solution of 130 mg (0.31 mmol) of N-[4-phenylsulfonyl)benzyl]-N-methyl-4,5-diaminonaphthalene in 3 ml acetic anhydride was allowed to react for 10 minutes. The acetic anhydride was removed in vacuo. The resulting residue was dissolved in 25 ml ethyl acetate and washed with saturated aqueous $NaHCO_3$ (2×20 ml). The organic layer was dried (anhydrous $MgSO_4$), and the solvent was removed under reduced pressure. The residue was flash chromatographed on silica, eluting with $CH_2Cl_2$:$CH_3OH$ (15:1). To remove co-eluting impurities, a second flash column was run, eluting with EtOAc:MeOH (19:1). In this manner, there was obtained a light brown oil which, when recrystallized from $CH_3OH$, yielded 75 mg (20%) of a light tan solid: m.p. 141 (decomp.); IR (KBr) broad 3500–2740, 1610, 1405, 1365, 1305, 1150, 1100 $cm^{-1}$; NMR ($CDCl_3$) δ 2.14 (s,3H), 2.62 (s,3H), 4.13 (s,2H), 6.5 (bs,2H), 6.86 (d,1H,J=7.8 Hz), 7.18 (t,1H,J=8.0 Hz), 7.37 (d,1H,J=8.6 Hz), 7.48–7.60 (m,5H), 7.89 (d,2H,J=8.3 Hz), and 7.95 (m,2H). High Res. Mass Spec. Calcd. for $C_{26}H_{23}N_3O_2S$: 441.1511. Found: 441.1528.

Example 17

Determination of Inhibition Constants Against 5,10-Methylene-Tetrahydrofolate Thymidylate synthase inhibition constants $K_i$ were determined by the following method. All assays were run at 25° C. and initiated by the addition of three different types of thymidylate synthase ("TS"): (1) *Escherichia Coli* TS ("ETS"); (2) *Candida* TS ("CTS"), a fungus; and (3) human TS ("HTS").

TS has ordered bireactant kinetics (Daron, H. H. and Aull, J. L., J. Biol. Chem. 253, 940–9451 (1978)), and the dUMP (2'-deoxyuridine-5'-monophosphate) concentration used for these reactions was near saturation levels so that the assays were pseudo-single substrates. All reaction mixtures contained 50 mM Tris at pH 7.8 (the final pH of the reaction was; 7.6), 10 mM DTT (dithiothreitol), 1 mM EDTA (ethylenediaminetetraacetic acid), 25 mM $MgCl_2$, 15 mM $H_2CO$ (formaldehyde) and 25 microM dUMP. When human TS was assayed, 100 micrograms/ml of BSA (bovine serum albumin) was present in the reactions. The range of THF (Tetrahydrofolate) was 5 to 150 microM (eight concentrations: 5, 6.6, 10, 13, 16, 25, 50 and 150 microM). A standard curve in the absence of inhibitor was run with each experiment. Three curves were then run with inhibitor at three different concentrations with a minimal range, where possible, from ½ to 2 times the $K_i$ (Cleland, W. W., Biochem. Biophys. Acta 67, 173–187 (1963)). These assays were done on a spectrophotometer at 340 nm (Wahba, A. J. and Friedkin, M., J. Biol. Chem. 236, PC11–PC12 (1961)) following the formation of DHF (dihydrofolate); mM extinction coefficient of 6.4) or by following the release of tritium (Lomax, M. I. S. and Greenberg, G. R., J. of Biol. Chem., 242, 109–113 (1967)) from the 5-position of dUMP (assays for tritium release contained 0.5 microI dUMP). Charcoal was used to remove unreacted dUMP from the tritium release reaction mixtures, and the resultant water was counted to determine the extent of reaction. Inhibition constants were then determined by plotting the apparent $K_m$ or the reciprocal of the apparent $V_{max}$ against the inhibitor concentration (Cleland, W. W., The Enzymes 2, 1–65 (1970)).

In Vitro Testing

Cellular growth in the presence of the compounds according to the present invention was assessed using three cell lines: the L1210 murine leukemia (ATCC CCL 219); CCRF-CEM, a human lymphoblastic leukemia line of T-cell origin (ATCC CCL 119); and a thymidine kinase deficient human adenocarcinoma line ($GC_3$/M TK$^-$). Both lines were maintained in RPMI 1640 medium containing 5% heat-inactivated fetal bovine serum without antibiotics.

$IC_{50}$ values were determined in 150 microliter microcultures each containing 1500 (L1210), 4000 (CCRF-CEM) or 10,000 ($GC_3$/M TK$^-$) cells established in 96 well plates in growth medium supplemented with 50 IU/ml penicillin and 50 mcg/ml streptomycin. Growth was measured over 3 days (L1210) or 5 days (CCRF-CEM and $GC_3$/M TK$^-$ of continuous exposure to varying concentrations of each test compound added 4 hours after initial cell plating by the MTT-tetrazolium reduction assay of Mosmann (T. J. Immunol. Meth. 65, 55–63 (1983)), modified according to Alley et al. (Cancer Res. 48, 589–601 (1988). Water insoluble derivatives were dissolved in DMSO and diluted as a final concentration of 0.3% solvent in cell cultures.

The results obtained from these procedures are tabulated below in Table 2, wherein the compounds tested had the following formula:

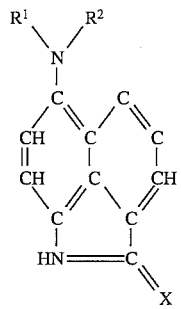

TABLE 1

(Compound Structures)

| Cmpd # | X | R1 | R2 |
|---|---|---|---|
| 5 | O | —$CH_2CH_3$ | —$CH_2$—⟨phenyl⟩—$SO_2N$⟨piperazine⟩$NH_2^+Cl^-$ |
| 6 | S | —$CH_2CH_3$ | —$CH_2$—⟨phenyl⟩—$SO_2N$⟨piperazine⟩NH |
| 8 | O | —$CH_2CH_3$ | —$CH_2$—⟨phenyl⟩—$SO_2$—⟨phenyl⟩ |
| 16 | O | —$CH_2CH_2OH$ | —$CH_2$—⟨phenyl⟩—$SO_2N$⟨piperazine⟩NH |

TABLE 1-continued (Compound Structures)

| Cmpd # | X | R1 | R2 |
|---|---|---|---|
| 19 | O | —CH₂CH₂CH₃ | —CH₂—C₆H₄—SO₂N(piperazine)NH |
| 22 | O | —CH(CH₃)₂ | —CH₂—C₆H₄—SO₂N(piperazine)NH |
| 40 | O | —CH₂CH₂CH₂OH | —CH₂—C₆H₄—SO₂N(piperazine)NH |
| 41 | H,H | —CH₂CH₃ | —CH₂—C₆H₄—SO₂—C₆H₅ |
| 24 | O | —CH₂SCH₃ | —CH₂—C₆H₄—SO₂—C₆H₅ |
| 27 | O | —CH₃ | —CH₂—C₆H₄—SO₂N(piperazine)NH |
| 29 | O | —CH₃ | —CH₂—C₆H₄—SO₂—C₆H₅ |
| 34 | NH | —CH₂CH₃ | —CH₂—C₆H₄—SO₂—C₆H₅ |
| 31 | O | —CH₃ | —CH₂-(1,4-naphthyl)-CH₂OH |
| 37 | NH | —CH₃ | —CH₂—C₆H₄—SO₂—C₆H₅ |
| 47 | O | —CH₃ | —CH₂-(2,6-naphthyl)-CH₂OH |

TABLE 2

| | (Compound Properties) | | | | | |
|---|---|---|---|---|---|---|
| | Ki (μM) | | | IC50 (μM) | | |
| Cmpd # | ETS | HTS | CTS | L1210 | (CRFCEM) | GC3-M |
| 5 | 42 ± 15 | 1.7 ± 0.8 | 29 ± 4 | 6 | 4.1 | 16 |
| 6 | 50 ± 9 | 3.4 ± 0.4 | 23 ± 15 | 2.1 | 3.5 | >5 |
| 8 | >1 | 1.2 ± 0.4 | >1 | 3.05 | >3.33 | >3.33 |
| 16 | 14 ± 7 | 0.87 ± 0.19 | 11 ± 7 | 50 | 31 | >50 |
| 19 | >20 | 12 ± 4 | >10 | 2.9 | 3.1 | 5.4 |
| 22 | 23 ± 7 | 4.9 ± 0.7 | 43 ± 9 | 3.9 | 6.8 | 5.9 |
| 40 | >10 | 11 ± 5 | >10 | 21.5 | 15.0 | 30.0 |
| 41 | >5 | 12 ± 3 | >10 | Not Done | Not Done | Not Done |
| 24 | >1 | 3.9 ± 1.7 | >1 | 2.1 | 2.8 | >10 |
| 27 | 31 ± 15 | 0.55 ± 0.34 | 14 ± 1 | 2.3 | 8.3 | 25.0 |
| 29 | >1 | 0.71 ± 0.27 | >1 | 4.2 | 3.5 | >5.0 |
| 34 | 10 ± 6 | 0.075 ± 0.037 | 0.38 ± 0.11 | 0.7 | 1.25 | 3.0 |
| 31 | >2 | 10 ± 1 | >2 | 0.8 | 3.0 | 4.0 |
| 37 | 2.9 ± 1.0 | 0.021 ± 0.003 | 0.15 ± 0.04 | 0.38 | 1.6 | 4.6 |
| 47 | >10 | 20 ± 10 | >10 | 1.7 | >4 | >4 |

While the invention has been described in detail and with reference to specific embodiments thereof, it will be apparent to one skilled in the art that various changes and modifications can be made therein without departing from the spirit and scope thereof. Thus, it is intended that the present invention cover the modifications and variations of this invention provided they come within the scope of the appended claims and their equivalents.

We claim:

1. A compound of the formula

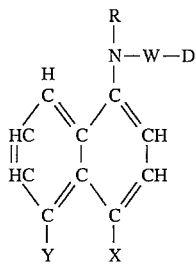

wherein:

W is an alkylene group;

D is a structure having two rings which are fused or linked via a linking group —$SO_2$— that are unsubstituted or substituted, where (i) one ring is a phenyl ring and (ii) the other ring is a phenyl ring or a 6-membered heterocyclic ring;

R is a hydrogen atom or an alkyl group; and

X and Y together form

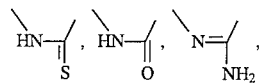

-continued

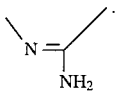

; or a pharmaceutically acceptable salt thereof.

2. A compound or a pharmaceutically acceptable salt thereof according to claim 1, wherein W is an unsubstituted alkylene group.

3. A compound or a pharmaceutically acceptable salt thereof according to claim 2, wherein W is —$(CH_2)$—.

4. A compound or a pharmaceutically acceptable salt thereof according to claim 1, wherein X and Y together form

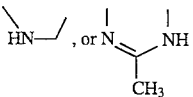

5. A compound or a pharmaceutically acceptable salt thereof according to claim 1, wherein D is

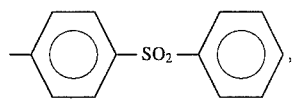

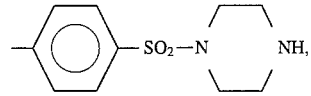

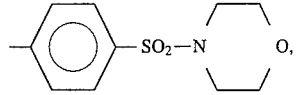

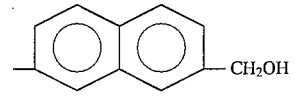

-continued or

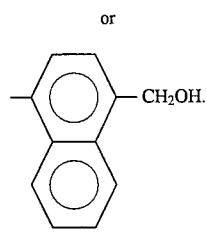

6. A compound or a pharmaceutically acceptable salt thereof according to claim 5, wherein R is —CH₃, —CH₂CH₃, —CH₂CH₂OH, —CH₂CH₂CH₃, —CH(CH₃)₂, —CH₂SCH₃ or —CH₂CH₂CH₂OH.

7. A compound of the formula

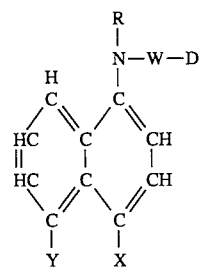

wherein:
W is an alkylene group;
D is a structure having two rings which are fused or linked via a linking group —SO₂— that are unsubstituted or substituted, where (i) one ring is a phenyl ring and (ii) the other ring is a phenyl ring or a 6-membered heterocyclic ring;
R is a hydrogen atom or an alkyl group; and
X and Y together form part of a pyrimidine, pyrrolidine or pyrrole ring;
or a pharmaceutically acceptable salt thereof.

8. A compound or a pharmaceutically acceptable salt thereof according to claim 1, wherein the two rings of D are bonded through an —SO₂— group.

9. A compound or a pharmaceutically acceptable salt thereof according to claim 8, wherein said heterocyclic ring contains a nitrogen heteroatom bonded to the —SO₂— group.

10. A compound or a pharmaceutically acceptable salt thereof according to claim 9, wherein said heterocyclic ring further contains another nitrogen heteroatom or an oxygen heteroatom.

11. A compound or a pharmaceutically acceptable salt thereof according to claim 10, wherein said other ring (ii) of D is a phenyl ring.

12. A compound or a pharmaceutically acceptable salt thereof according to claim 1, wherein R is —CH₃, —CH₂CH₃, —CH₂CH₂OH, —CH₂CH₂CH₃, —CH(CH₃)₂, —CH₂SCH₃ or —CH₂CH₂CH₂OH.

13. A compound or a pharmaceutically acceptable salt thereof according to claim 1, wherein:
W is —(CH₂)—;

D is

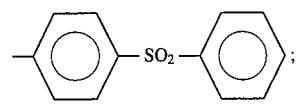

and
X and Y together form

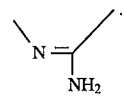

14. A compound or a pharmaceutically acceptable salt thereof according to claim 13, wherein R is —CH₃ or —CH₂CH₃.

15. A compound or a pharmaceutically acceptable salt thereof according to claim 14, wherein R is —CH₃.

16. A compound or a pharmaceutically acceptable salt thereof according to claim 6, wherein D is

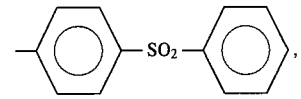

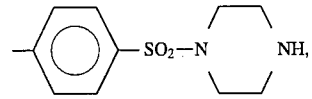

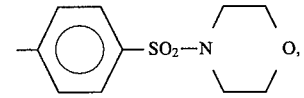

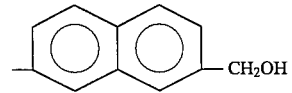

or

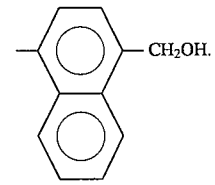

17. A compound or a pharmaceutically acceptable salt thereof according to claim 16, wherein W is —(CH₂)—.

18. A pharmaceutical composition comprising a compound or a pharmaceutically acceptable salt thereof according to claim 7 in an amount effective to inhibit thymidylate synthase, and a pharmaceutically acceptable carrier or diluent.

19. A pharmaceutical composition comprising a compound or a pharmaceutically acceptable salt thereof according to claim 1 in an amount effective to inhibit thymidylate synthase, and a pharmaceutically acceptable carrier or diluent.
20. A pharmaceutical composition according to claim 19, wherein D is
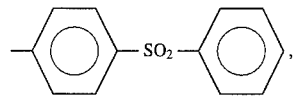
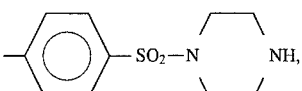
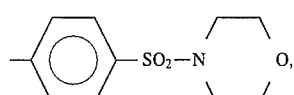
-continued
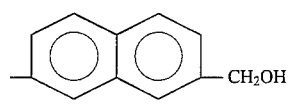
or
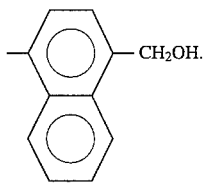
* * * * *

UNITED STATES PATENT AND TRADEMARK OFFICE
CERTIFICATE OF CORRECTION

PATENT NO.: 5,574,039

DATED: November 12, 1996

INVENTOR(S): Michael D. VARNEY et al.

It is certified that an error appears in the above-identified patent and that said Letters Patent is hereby corrected as shown below:

Col. 5, between lines 56-65, the formula,

"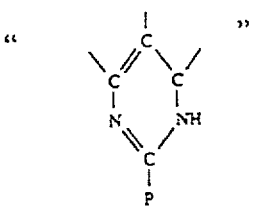"

should instead read

-- 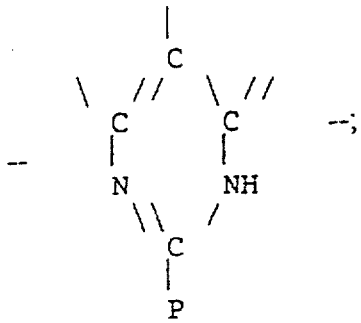 --;

Col. 19, line 40, after "(0.260 mol)", insert --70%--;

line 56, "vaporated" should read --evaporated--;

UNITED STATES PATENT AND TRADEMARK OFFICE
CERTIFICATE OF CORRECTION

PATENT NO.: 5,574,039

DATED: November 12, 1996

INVENTOR(S): Michael D. VARNEY et al.

It is certified that an error appears in the above-identified patent and that said Letters Patent is hereby corrected as shown below:

Col. 41-42, between lines 1 and 30, the following reaction scheme

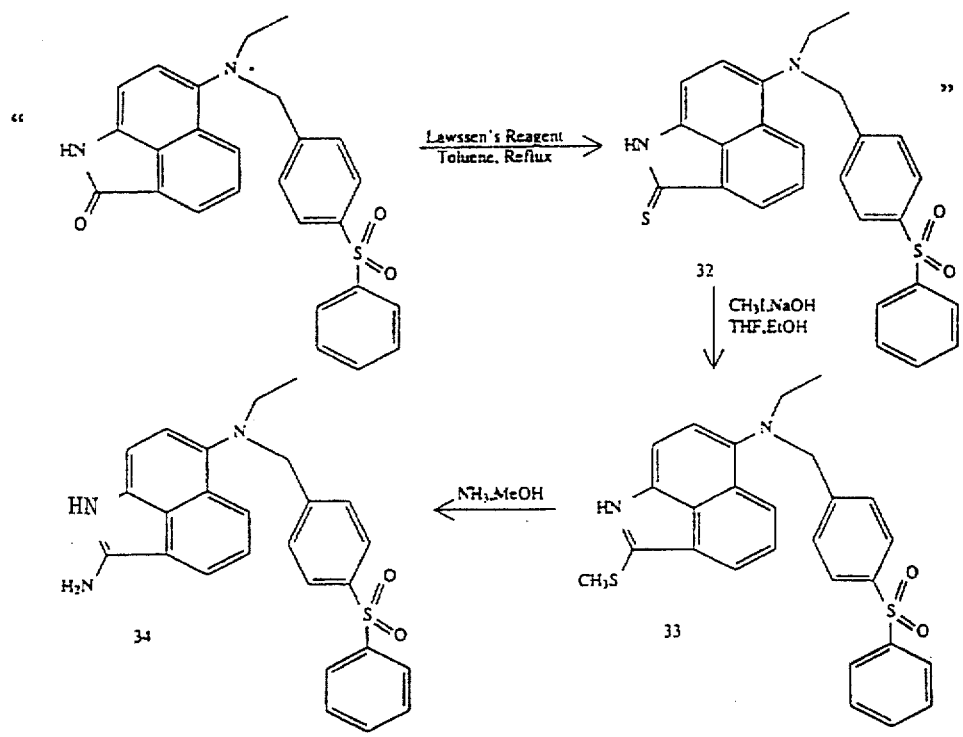

UNITED STATES PATENT AND TRADEMARK OFFICE
CERTIFICATE OF CORRECTION

PATENT NO.:     5,574,039

DATED:          November 12, 1996

INVENTOR(S):    Michael D. VARNEY et al.

It is certified that an error appears in the above-identified patent and that said Letters Patent is hereby corrected as shown below:

should instead read

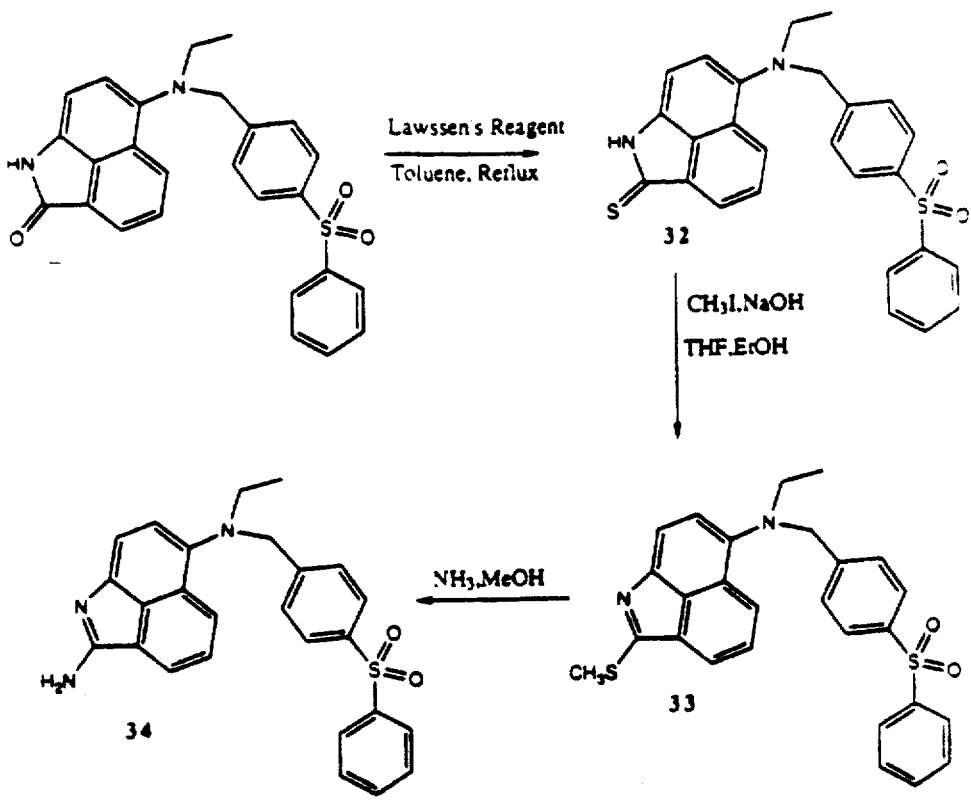

UNITED STATES PATENT AND TRADEMARK OFFICE
CERTIFICATE OF CORRECTION

PATENT NO.: 5,574,039

DATED: November 12, 1996

INVENTOR(S): Michael D. VARNEY et al.

It is certified that an error appears in the above-identified patent and that said Letters Patent is hereby corrected as shown below:

Cols. 43-44, between lines 1 and 30, the following reaction scheme

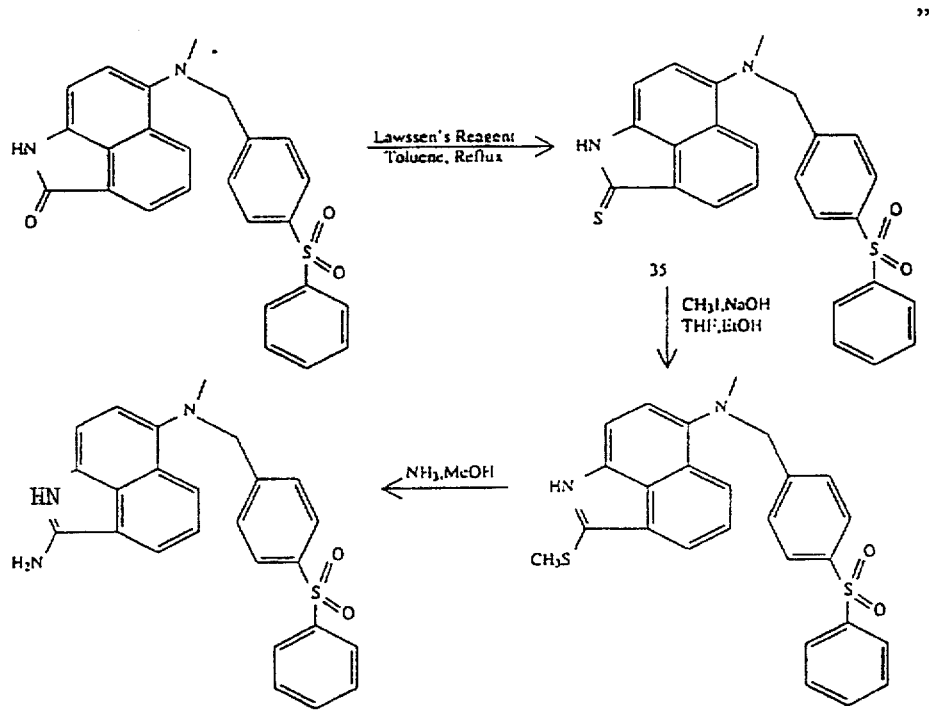

United States Patent and Trademark Office
CERTIFICATE OF CORRECTION

Page 5 of 6

PATENT NO.: 5,574,039

DATED: November 12, 1996

INVENTOR(S): Michael D. VARNEY et al.

It is certified that an error appears in the above-identified patent and that said Letters Patent is hereby corrected as shown below:

should instead read

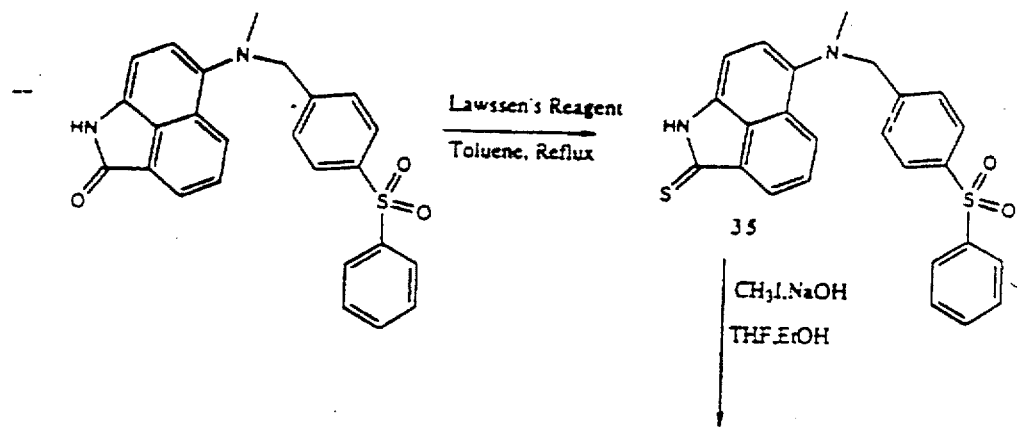

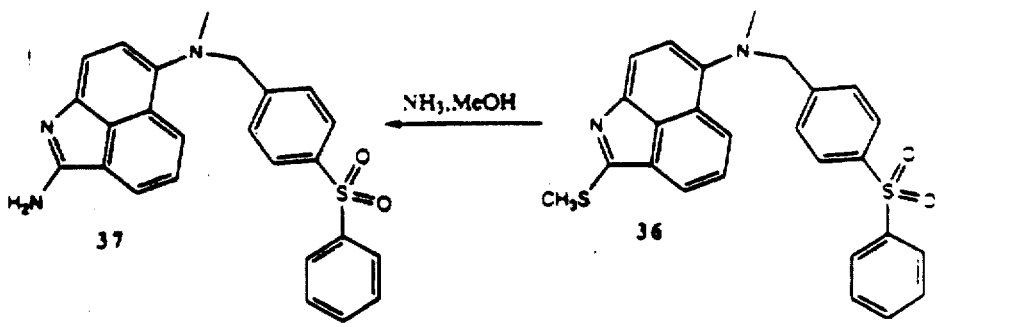

UNITED STATES PATENT AND TRADEMARK OFFICE
CERTIFICATE OF CORRECTION

PATENT NO.: 5,574,039

DATED: November 12, 1996

INVENTOR(S): Michael D. VARNEY et al.

It is certified that an error appears in the above-identified patent and that said Letters Patent is hereby corrected as shown below:

Claim 16, col. 62, line 21, "claim 6" should read --claim 7--.

Signed and Sealed this

Fifteenth Day of July, 1997

*Attest:*

BRUCE LEHMAN

*Attesting Officer*  *Commissioner of Patents and Trademarks*